US012306176B2

United States Patent
Garg et al.

(10) Patent No.: US 12,306,176 B2
(45) Date of Patent: May 20, 2025

(54) MICROFLUIDIC BI-DIRECTIONAL MIGRATION ASSAY

(71) Applicant: Ohio State Innovation Foundation, Columbus, OH (US)

(72) Inventors: Ayush Garg, Columbus, OH (US); Travis Jones, Columbus, OH (US); Sarah Bushman, Columbus, OH (US); Jessica Ferree, Columbus, OH (US); Vishwanath Subramaniam, Columbus, OH (US); Jonathan Song, Columbus, OH (US); Deepa Subramaniam, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 1343 days.

(21) Appl. No.: 16/650,950

(22) PCT Filed: Oct. 18, 2018

(86) PCT No.: PCT/US2018/056502
§ 371 (c)(1),
(2) Date: Mar. 26, 2020

(87) PCT Pub. No.: WO2019/079589
PCT Pub. Date: Apr. 25, 2019

(65) Prior Publication Data
US 2020/0290039 A1     Sep. 17, 2020

Related U.S. Application Data

(60) Provisional application No. 62/573,908, filed on Oct. 18, 2017.

(51) Int. Cl.
G01N 33/50     (2006.01)
B01L 3/00      (2006.01)
(Continued)

(52) U.S. Cl.
CPC .... G01N 33/5029 (2013.01); B01L 3/502761 (2013.01); C12M 23/22 (2013.01);
(Continued)

(58) Field of Classification Search
CPC .......... G01N 33/5029; G01N 33/5011; G01N 33/57415; B01L 3/502761; B01L 2300/06;
(Continued)

(56) References Cited

U.S. PATENT DOCUMENTS 5,945,008 A  *  8/1999  Kisakibaru ....... H01J 37/32697
                                                204/192.12
2012/0252111 A1   10/2012  Tono et al.
(Continued)

FOREIGN PATENT DOCUMENTS

WO     2012138882 A2    10/2012
WO     2013126774 A2     8/2013
(Continued)

OTHER PUBLICATIONS

International Search Report issued for PCT/US2018/056502, mailed Jan. 8, 2019.

*Primary Examiner* — John McGuirk
(74) *Attorney, Agent, or Firm* — Thomas | Horstemeyer, LLP

(57) ABSTRACT

Disclosed herein are devices and methods for measuring the effect of chemokines and electric fields on cell migration. This approach is inherently non-contact and does not require injection of current. For example, disclosed herein is a device for assessing cell migration that comprises a cell migration chamber and an electromagnet positioned to produce a uniform electric field across the length of the chamber. Also disclosed is a method for assaying a cell that involves loading cells into the disclosed device along with a
(Continued)

chemokine in an amount to produce a chemokine gradient, activating the electromagnet to produce an electric field across the cell migration chamber, and imaging the cells to measure the dual effect of the chemokine and the electric field on the cells.

19 Claims, 29 Drawing Sheets

(51) Int. Cl.
    *C12M 1/00*         (2006.01)
    *C12M 1/34*         (2006.01)
    *C12M 1/42*         (2006.01)

(52) U.S. Cl.
    CPC ............ *C12M 35/02* (2013.01); *C12M 41/46* (2013.01); *G01N 33/5011* (2013.01); *B01L 2300/06* (2013.01); *B01L 2300/0809* (2013.01); *B01L 2300/12* (2013.01); *B01L 2400/0415* (2013.01)

(58) Field of Classification Search
    CPC ......... B01L 2300/0809; B01L 2300/12; B01L 2400/0415; B01L 2200/0652; B01L 2300/0877; B01L 2300/16; C12M 23/22; C12M 35/02; C12M 41/46
    See application file for complete search history.

(56) References Cited

U.S. PATENT DOCUMENTS

| | | | |
|---|---|---|---|
| 2015/0147821 A1* | 5/2015 | Sing | G01N 33/54326 422/69 |
| 2015/0353916 A1* | 12/2015 | Subramaniam | C12N 13/00 435/39 |
| 2017/0022464 A1 | 1/2017 | Novak et al. | |

FOREIGN PATENT DOCUMENTS

| | | |
|---|---|---|
| WO | 2015138032 A2 | 9/2015 |
| WO | 2016077067 A2 | 5/2016 |

\* cited by examiner

MICROFLUIDIC BI-DIRECTIONAL MIGRATION ASSAY

CROSS-REFERENCE TO RELATED APPLICATIONS

This application is a National Stage of International Application No. PCT/US2018/056502, filed Oct. 18, 2018, which claims benefit of U.S. Provisional Application No. 62/573,908, filed Oct. 18, 2017, which is hereby incorporated herein by reference in its entirety.

BACKGROUND

Cell migration is a necessary step in the process of metastatic dissemination of tumor cells to local and distant sites (Gupta G P & Massagué J (2006) Cell 127 (4):679-695). It has been shown that tumor cells use similar migration mechanisms to those that occur in normal physiological processes such as wound healing, embryonic morphogenesis, and immune cell trafficking (Friedl P & Wolf K (2003) Nat Rev Cancer 3 (5):362-374). In these processes, external chemical and electrical cues are not only responsible for initiating the migration but also for guiding the cells. Therefore, a fundamental understanding of the mechanisms by which migrating cells sense and respond to external stimuli would accelerate progress for both cell recruitment applications (e.g. wound repair and tissue organization) and in oncology (Cortese B, et al. (2014) lntegr Biol (Camb) 6 (9):817-830).

SUMMARY

Disclosed herein is the use of alternating magnetic fields to induce EFs in a cell migration assay. This approach is inherently non-contact and does not require injection of current. These EFs are referred to herein as induced EFs (iEFs). Unlike direct current EF (dcEF), iEFs periodically fluctuate in magnitude and direction. It is possible however, to create a net directional field effect by driving the magnetic field with an asymmetric signal.

Disclosed herein is a device for assessing cell migration that involves a cell migration chamber comprising an optically transparent material coated with a cell migration substrate, and an electromagnet positioned to produce a uniform electric field across the length of the chamber, thereby defining a positive end of the chamber and a negative end of the chamber.

In some embodiments, the cell migration substrate is fabricated into microtracks, for example, to replicate the topography of paths formed in tissues, such as by vessels, extracellular matrix fibers, or white matter tracts in the brain. For example, in some embodiments, the device involves a cell port in the middle of the chamber configured to receive cells, a first media port at the positive end of the chamber, and a second media port at the negative end of the chamber, a plurality of microtracks fluidly connecting the cell port to the first media port, and a plurality of microtracks fluidly connecting the cell port to the second media port.

The cell migration substrate can be any hydrogel capable of mimicking tissue environments, such as an extracellular matrix (ECM). A variety of natural and synthetic polymers have been used to fabricate hydrogels. Collagen, hyaluronic acid, chondroitin sulfate, fibrin, fibronectin, alginate, agarose, chitosan, and silk have been the most commonly used natural polymers used. Among all these natural polymers, collagen has been the most widely investigated since it is the most abundant structural protein of ECM in multiple tissues. Synthetic biodegradable polymers, such as poly(ethylene glycol), poly(lactic acid), poly(glycolic acid), and a copolymer poly(lactic-glycolic) acid have also been used for engineered scaffolds.

The width of these microtracks can be selected based on the environment being mimicked. For example, in some cases, the microtracks are about 1 to 100 μm in width, such as 10, 20, 30, 40, or 50 μm in width.

The electromagnet can be any device capable of creating a time varying magnetic field from an alternating current source or be produced by a capacitive arrangement with a DC or AC applied voltage across voltages placed outside (and not in contact) with the medium or medium containing the cells. For example, in some embodiments, the electromagnet comprises a Helmholtz coil. In some embodiments, the electromagnet produces an electric field (iEF) of about 1 to 10V/cm, including 1, 2, 3, 4, 5, 6, 7, 8, 9, or 10V/cm.

The device is preferably sized to fit on a microscope stage for imaging. Therefore, the device can also contain a microscope positioned to generate time-lapse images of cells in the cell migration chamber. Likewise, the device also preferably contains a viewing window to observe the cells. For example, when a Helmholtz coil is used, the coils can be spaced to create a viewing window for the chamber.

The device can contain a single cell migration chamber, or a plurality of cell migration chambers, including 2, 4, 6, 8, 10, 12, 24, 36, 48, or 100 chambers.

Any optically transparent material suitable for producing cell culture dishes can be used. In some embodiments, the optically transparent material is a glass, quartz, or a plastic. In some embodiments, the optically transparent material comprises polydimethylsiloxane (PDMS). In some embodiments, the optically transparent material comprises polymethyl methacrylate (PMMA).

Also disclosed herein is a method for assaying a cell that involves providing the device disclosed above, loading cells into the cell port, loading a first medium into the first media port and a second medium into the second media port, wherein at least one of the first medium or the second medium comprises a chemokine in an amount to produce a chemokine gradient, activating the electromagnet to produce an electric field across the cell migration chamber, and imaging the cells to measure the dual effect of the chemokine and the electric field on the cells. In some embodiments, the disclosed method further involves repeating the steps with the chemokine gradient going in the opposite direction. The method can also further involve loading a candidate agent into one of the cell port, first media port, or second media port to evaluate the effect of the candidate agent on cell migration.

In some embodiments, the cell is a cancer cell. Therefore, in these embodiments, the candidate agent comprises a candidate inhibitor of metastasis. The cancer of the disclosed methods can be any cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The chemokine used in the disclosed method can be any agent, or combination of agents, capable of mimicking a chemoattractant produced by a cell to be targeted, such as a cancer cell. Numerous studies have demonstrated that chemokines and their receptors are involved in tumor cell growth and progression. Tumor cells express selected chemokine receptors, which can help direct tumor cells to specific anatomic sites to form metastases. These sites of metastasis produce particular chemokines that attract circulating tumor cells into a 'premetastatic niche', which has a supporting microenvironment for the growth of metastatic tumor cells. In some embodiments the chemokine is epidermal growth factor (EGF).

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a schematic of a cell migration chamber for use in the disclosed MBDM assay. Cells are seeded in the center port and are tracked as they migrate to the outer ports through the microtracks connecting them. FIG. 1B is a top view of an example MBDM assay device. FIG. 1C is an isometric view of an embodiment MBDM assay device. FIG. 1D is a cross-section cut (plane marked with dotted line in FIG. 1C) indicating the location of an embodiment MBDM assay device and its relative position with the microscope objective. FIG. 1E shows cells from the center port can migrate into the opposing microtracks and migrate either towards the top or bottom media ports and under the influence of iEFs applied either parallel or anti-parallel to the direction of cell migration. FIG. 1F shows time-lapse images of GFP-tagged MDA-MB-231 cell migrating through a single microtrack.

FIG. 2A shows iEFs applied anti-parallel to the direction of migration increased migration speeds by 46% compared to untreated controls but had no effects when applied parallel to the direction of migration. Treatment with the Akt inhibitor, MK2206, nullified this directional response to iEF. Thus, Akt phosphorylation is required for directional response of MDA-MB-231 cells to iEFs. FIG. 2B shows iEFs increased cell persistence when applied parallel or anti-parallel to the direction of migration. MK2206 treatment significantly downregulated their ability to sustain directed migration. All data is presented as mean±SEM. N=3 for each condition with a minimum of 60 cells in each condition. *$p<0.05$, $p<0.01$, *$p<0.005$, and ****$p<0.001$ (Pair-wise Student t-test).

FIG. 3A shows iEFs applied parallel to the direction of migration decreased migration speeds by 21% compared to cells migrating under EGF-gradients but iEFs had no effect when applied antiparallel to the direction of migration. Combined iEF (parallel) treatment with MK2206 reduced migration speeds by 40% compared to cells migrating under EGF-gradients. FIG. 3B shows iEFs had no effect (parallel or anti-parallel) on persistence of cells migrating under EGF gradients but MK2206 treatment again impaired their ability to sustain directed migration. All data is presented as mean±SEM. N=3 for each condition with a minimum of 60 cells in each condition. *$p<0.05$, $p<0.01$, *$p<0.005$, and ****$p<0.001$ (Pair-wise Student t-test).

FIG. 4A shows representative immunofluorescence images of MDA-MB-231 cells stained for F-actin with phalloidin and nuclei with DAPI. The F-actin distribution under different treatment conditions was quantified with the custom MATLAB script that plotted the relative weighted intensity of actin with respect to the geometric center for each cell onto a rose plot. Polarization ratio was then calculated for every individual cell. FIG. 4B shows quantification of the F-actin polarization ratio (minimum, 1st quartile, median, 3rd quartile, and maximum). N=3 for each condition with a minimum of 30 cells in each condition. *$p<0.05$ (Pair-wise non-parametric Wilcoxon Test).

FIG. 5A contains representative immunofluorescence images. Arrows point to EGFR clusters. Scale bar is 20 µm. FIG. 5B shows Western blot analysis indicating that iEFs downregulate EGFR phosphorylation in EGF-treated cells. FIG. 5C shows densitometry analysis for phosphorylated EGFR (p-EGFR) levels. FIG. 5D shows densitometry analysis for total EGFR (t-EGFR) levels. FIG. 5E shows ratio of p-EGFR to t-EGFR levels. All data presented as mean±SEM. All data pooled from three independent biological replicates for each condition. *$p<0.05$, $p<0.01$, *$p<0.005$, and ****$p<0.001$ (Pair-wise Student t-test).

FIG. 6A shows LDH activity was unchanged after 12 hours of iEF treatment. EGF treatment slightly lowered LDH activity but was not significant. iEF treatment in combination with EGF did not change LDH activity as compared to the control case or EGF treatment alone. FIG. 6B shows SDH activity was unchanged after 12 hours of iEF treatment compared to control. EGF treatment increased SDH activity but was not significant compared to control. Interestingly, iEF treatment in combination with EGF showed a decrease in SDH activity that was significantly different from EGF treatment alone but not control. All data presented as mean±SEM. (Pair-wise Student t-test, *$p<0.05$, $p<0.01$, *$p<0.005$, and ****$p<0.001$, all data was pooled from three independent biological replicates for each condition.

FIG. 7A, Top shows red peak is aligned anti-parallel (↓) to the direction of cell migration. FIG. 7A, Bottom shows iEFs applied parallel (↑) to the direction of migration as the red peak is in the same direction as cell migration. iEFs are applied at a frequency of 100 kHz and the graph is the variation of field for one time cycle (10 µs). FIG. 7B shows variation of iEFs at its peak value (the arrow-head in (FIG. 7A)). In the viewing window, peak strength is between ~60-80 μV/cm. FIG. 7C shows time-averaged asymmetry in iEF for one time cycle (10 μs) from (FIG. 7A, Bottom) showing the average magnitude iEFs in parallel (↑) and anti-parallel (↓) directions.

FIG. 8A shows iEF treatment had no effect on the total migration numbers when cells migrated in absence of exogenous EGF. However, iEFs bi-directionally reduced total migration numbers of cells migrating under EGF gradients. FIG. 8B shows representative images of the wells for all the conditions for the data represented in FIG. 8A. All data presented as mean±SEM (Pair-wise Student t-test, *p<0.05, p<0.01, *p<0.005, and ****p<0.001, N=3 for each condition).

FIG. 10A shows Western blot analysis to examine the expression of p-Akt (Ser473) and total Akt protein expression levels on treatment with EGF and iEFs. Clearly, iEF treatment had no direct effects on the activation of Akt in presence or absence of EGF (25 ng/mL). Moreover, the total Akt levels in these cells also remained unchanged on treatment with iEFs. FIG. 8B shows densitometry analysis of p-Akt (Ser-473) levels for the blots shown in FIG. 10A. FIG. 10C shows densitometry analysis of total Akt levels for the blots shown in FIG. 10A. All data presented as mean±SEM (Pair-wise Student t-test, *p<0.05, p<0.01, *p<0.005, and ****p<0.001, N=3 for each condition).

FIG. 11A, Left is an fluorescent intensity map from experimental images such as that shown in FIG. 11D using 10 kDa FITC conjugated dextran dye. FIG. 11A, Right is a mathematical model of gradients in the MBDM assay plotted using COMSOL Multiphysics 5.2a. FIG. 11A, Middle is a comparison of experimental (solid lines) to mathematical model (dotted lines) showing that they match each other closely. FIG. 11B is a comparison of numerical model to the experimental at 12 hours for a diffusion coefficient of $1 \times 10^{-12}$ m$^2$/s. FIG. 11C shows predicted range of diffusion coefficient by the numerical model. FIG. 11D shows representative region of interest in one microtrack used for experimental calculations. FIG. 11E shows change in average intensity of the dye over time in the microtracks. FIG. 11F shows normalized fluorescent intensity of dye over the length of the microtrack at the 12-hour time-point indicating a stable chemokine gradient in the MBDM assay.

FIG. 12A shows Western blot analysis to examine the expression of p-FAK (Tyr397) and total FAK protein expression levels on treatment with EGF and iEFs. Clearly, iEF treatment had no direct effects on the activation of FAK in presence or absence of EGF (25 ng/mL). Moreover, the total FAK levels in these cells also remain unchanged on treatment with iEFs. FIG. 12B shows densitometry analysis of p-FAK (Tyr-397) levels for the blots shown in FIG. 12A. FIG. 12C shows densitometry analysis of total FAK levels for the blots shown in FIG. 12A. All data presented as Mean±SEM (Pair-wise Student t-test, *p<0.05, p<0.01, *p<0.005, and ****p<0.001, N=3 for each condition).

FIG. 12A shows Helmholtz coil using simple circuit element model compared with measured values of impedance. FIG. 12B shows frequency response of Helmholtz coil using simple circuit model compared with measured values of impedance phase for varying frequency inputs. The two resonant peaks correspond to inner and outer segments of the coil.

FIG. 16A shows 100 kHz, 20 Vpp sinewave applied to the coil using a function generator. The magnetic field probe was located at the center of the coil. FIG. 16B shows 100 kHz, 20 Vpp sawtooth waveform applied to the coil using a function generator. The magnetic field probe was located at the center of the coil.

DETAILED DESCRIPTION

Figure 1A:
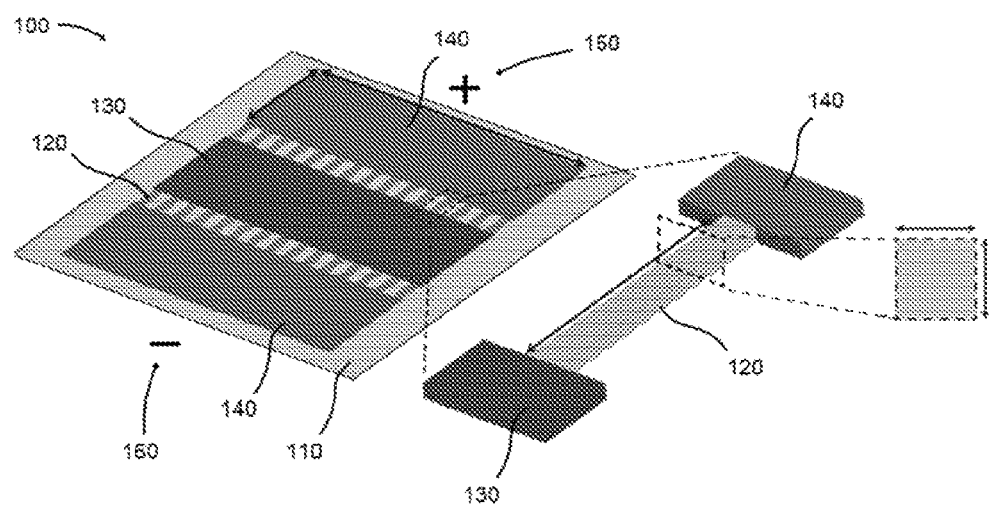
FIGS. 1A to 1F show an embodiment of the disclosed microfluidic bi-directional migration (MBDM) assay device for quantifying cell migration in response to iEF treatment.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

FIGS. 1A to 1D depict an embodiment of a disclosed microfluidic bi-directional migration (MBDM) assay. FIG. 1A depicts a cell migration chamber 100, which is composed of an optically transparent base 110. The cell migration chamber is designed to be exposed to an electric field across the length of the chamber, thereby defining a positive end 150 of the chamber and a negative end 160 of the chamber. The chamber 100 contains a cell port 130 in the middle of the chamber 100, a first media port 140 at the positive end 150 of the chamber, and a second media port 140 at the negative end 160 of the chamber, a plurality of microtracks 120 connecting the cell port 130 to the first media port 140, and a plurality of microtracks 120 connecting the cell port 130 to the second media port 140.

Figure 1B:
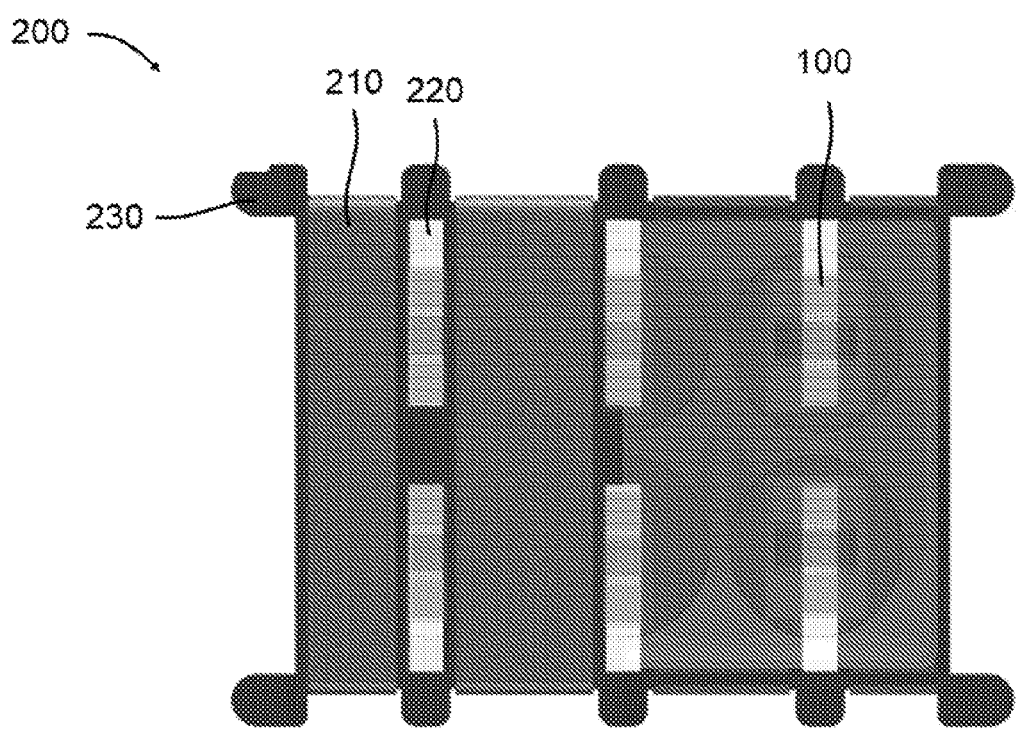
Figure 1C:
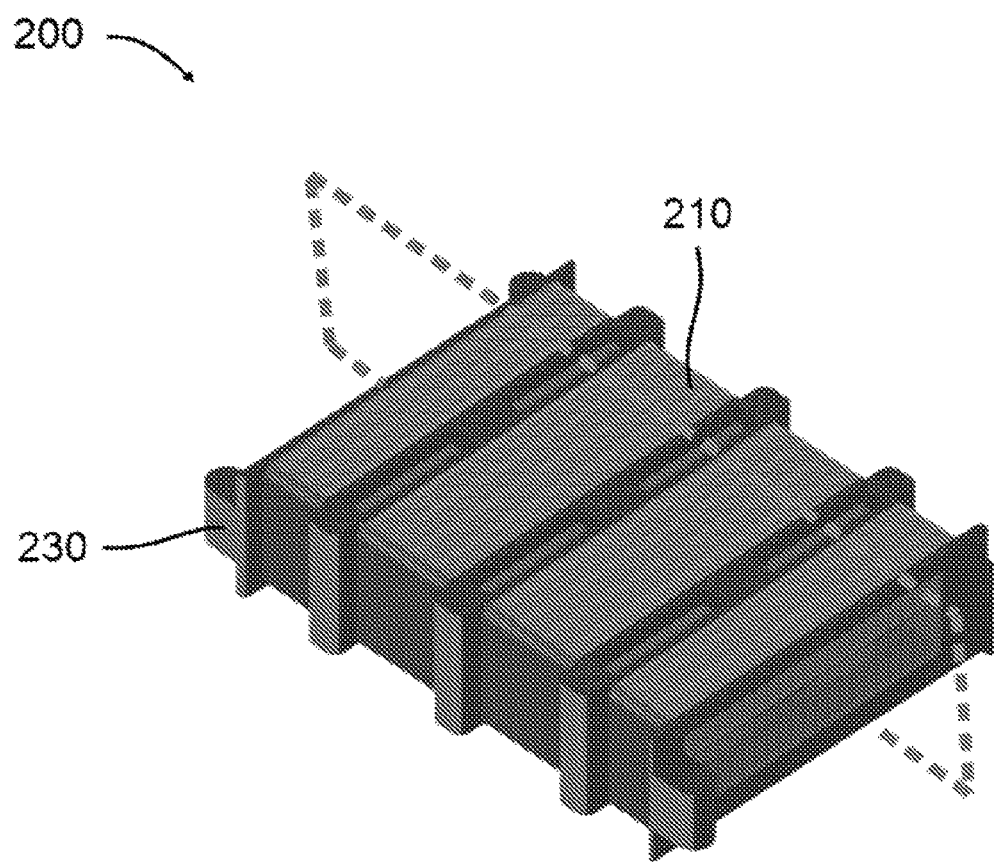

FIGS. 1B to 1C depict a device 200 that is composed of a housing 230 containing a plurality of cell migration chambers 100, sized to fit onto a microscope stage. The device 200 contains a Helmholtz coil 210 positioned to produce a uniform electric field across the length of the chamber 100. The device 200 is designed to be used with a microscope 240 to generate time-lapse images of cells in the cell migration chamber 100. Therefore, the Helmholtz coil 210 is spaced to create a viewing window 220 for the microscope 240.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Electric Fields Control the Motility of Metastatic Breast Cancer Cells

Induced EFs (iEFs) were produced by electromagnetic induction with a custom Helmholtz coil that was designed so that iEFs were oriented on average in one direction. It is important to note that unlike direct current EFs (dcEFs), iEFs do not inject electric currents into the medium containing the cells, which on its own can impart a potent directional cue on cell migration (Cohen D J, et al. (2014) Nat Mater. 13 (4):409). Moreover, due to the non-contact nature of the iEFs, no electrochemically produced species are introduced in the cell media that could potentially alter cell-signaling and cell responses independent of EFs and currents (Schopf A, et al. (2016) Bioelectrochemistry 109: 41-48). Therefore, application of iEFs enables isolation of the effects of EFs.

Directed migration can be characterized quantitatively by cell migration speed and persistence. Persistence is a dimensionless quantity that can be defined as the capacity to maintain on average a single direction of motion (Maiuri P, et al. (2015) Cell 161 (2):374-386; Irimia D & Toner M (2009) Integr Biol (Camb). 1 (8-9):506-512). A high persistence value may indicate a cells ability to maintain a polarized state while a low persistence can indicate frequent directional changes or lack of net migration all together, implicating an inability to strongly polarize (Petrie R J, et al. (2009) Nat Rev Mol Cell Biol. 10 (8):538).

To quantify the effects of iEF treatment on directed cell migration speed and persistence, a custom microfluidic bi-directional microtrack (MBDM) assay was developed that enables real-time monitoring with time-lapse microscopy of cell motility. The MBDM assay features parallel arrays of narrow microtracks (~20 μm width and height) which replicate the topography of pre-existing paths formed by vessels, extracellular matrix fibers, and white matter tracts in the brain that have been shown to help guide migrating cancer cells in vivo (Wolf K, et al. (2009) Semin Cell Dev Biol. 20 (8):931-941). Moreover, various cancer cell types (including breast) have exhibited spontaneous and persistent migration in in vitro microtracks of comparable dimensions (Irimia D & Toner M (2009) Integr Biol (Camb) 1 (8-9):506-512).

In this study, the EF sensing mechanisms of breast cancer cells in response to asymmetric iEFs (<100 μV/cm) was investigated. Using a MBDM assay, changes in the speed and persistence of spontaneously migrating MDA-MB-231 breast cancer cells were observed. This cell type was selected for these studies because it is a putative metastatic breast cancer cell line that is also responsive to gradients of a chemoattractant such as EGF (Wang S J, et al. (2004) Exp Cell Res 300 (1):180-189; Wu A, et al. (2013) Proc Natl Acad Sci U S A 110(40):16103-16108). Prior to each experiment, cells were seeded in the center port of the MBDM assay where they can exhibit bi-directional migration into the opposing collection chambers in response to an asymmetric iEF. This configuration enables direct comparison of cell movement in response to iEFs applied primarily with the direction of cell migration ("parallel") or against the direction of cell migration ("anti-parallel") within the same microfluidic device. Here, the field direction is defined as the direction that has the higher peak magnitude, as well as higher time-average field strength.

In the presence of iEFs, cell speed and persistence both increased in a direction dependent manner, demonstrating the cells' ability to sense a net field direction. Moreover, cell speed but not persistence lost the directional response when iEFs were applied in combination with an Akt inhibitor. In the presence of an epidermal growth factor (EGF) gradient, iEFs hindered cell migration speeds in a direction dependent manner. However, persistence was not affected by iEFs in the presence of an EGF gradient. Western blot analysis, enzymatic assays, and immunofluorescence showed that iEFs inhibit EGFR phosphorylation, adversely affect mitochondrial function, and disrupt actin polarization respectively. When iEFs were applied in combination with an Akt inhibitor in the presence of EGF, there was a significant reduction in cell speed and persistence that was well below the levels of untreated controls. Overall, these results demonstrate the ability of migrating breast cancer cells to sense not only the presence of iEFs but also the net direction of asymmetric iEFs. In addition, these results suggest that selective hindering of EGF-promoted cancer metastasis through synergistic treatment with iEFs and pharmacological inhibitors should be explored.

Results

Figure 1D:
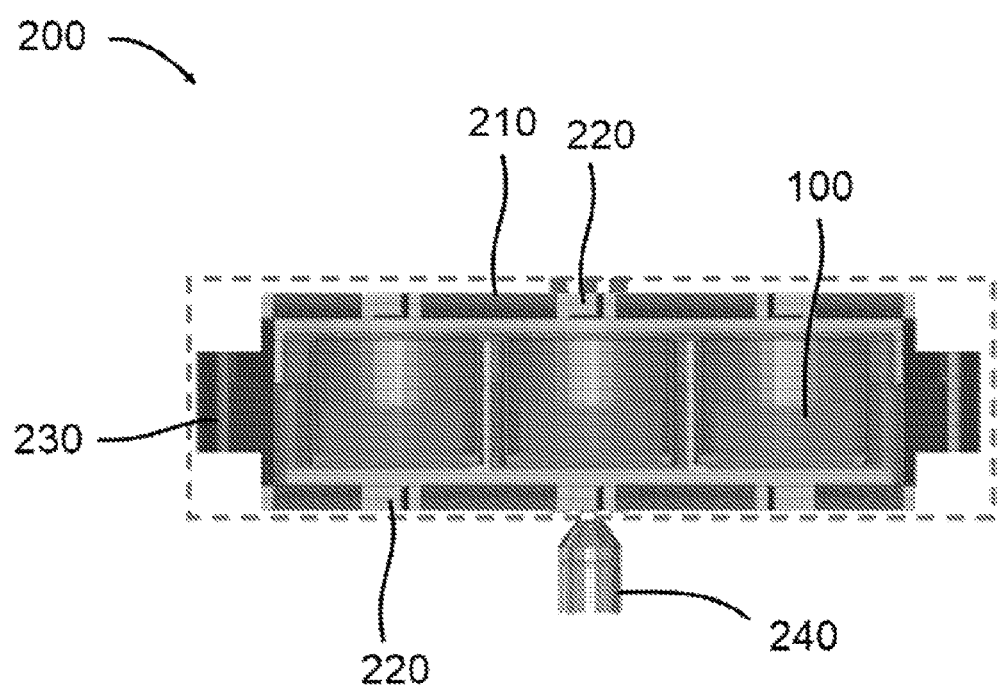
Figure 1E:
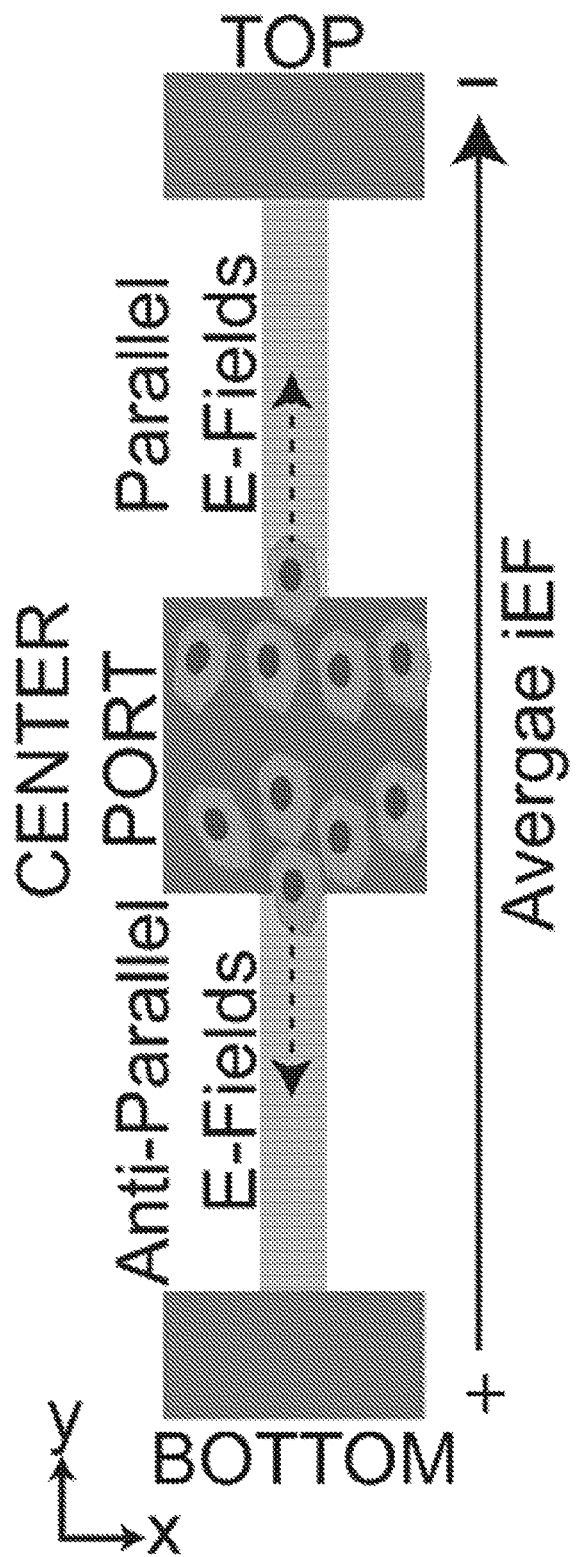
Figure 1F:
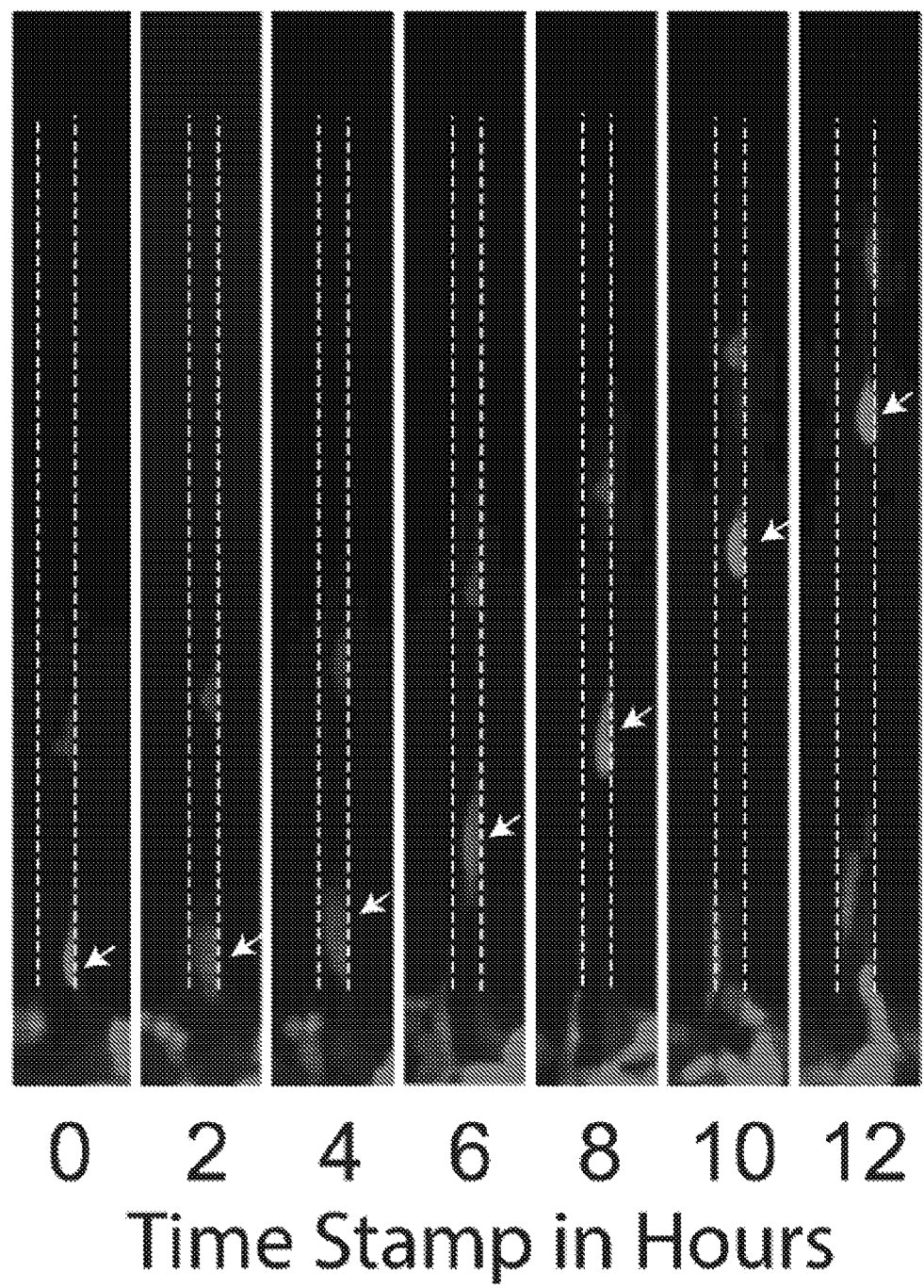
Figure 2A:
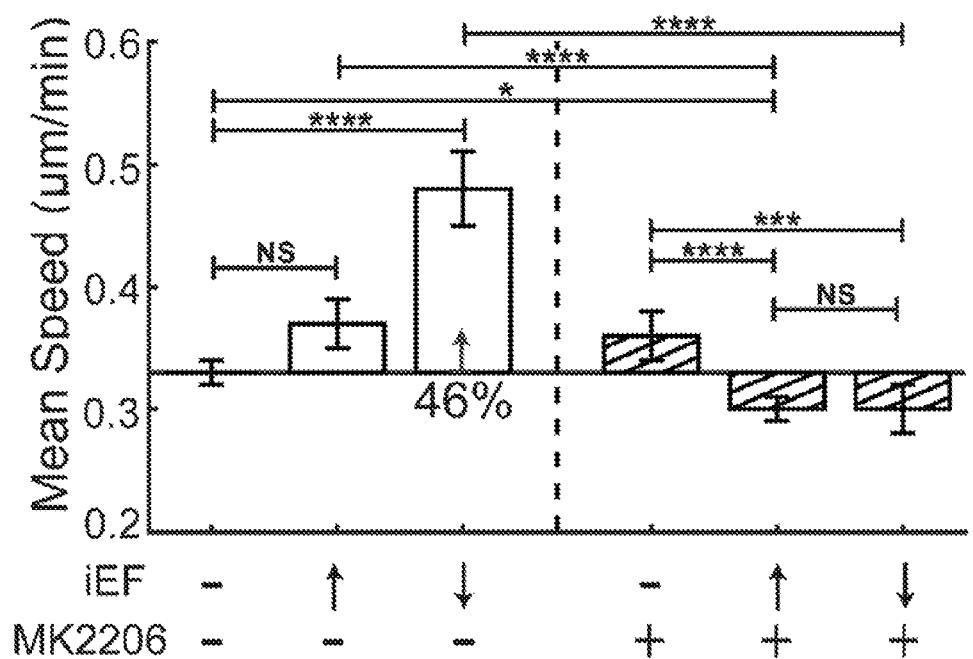
FIGS. 2A and 2B show iEF treatment increases the migration speeds of MDA-MB-231 migrating without exogenous EGF gradients.

Directional Electrotaxis of Breast Cancer Cells in Response to Induced Electric Fields The migration behaviors of MDA-MB-231 triple negative human breast cancer cells to standalone iEF treatment (FIGS. 1A-1C and 7) were first assessed within the custom MBDM assay (FIGS. 1D-1F). As expected, the MDA-MB-231 cells spontaneously migrated in the MBDM assay in the absence of any chemokine or inhibitor at a mean speed of 0.33 μm/min (FIG. 2A). iEF treatment alone and applied parallel to the direction of migration of the MDA-MB-231 cells resulted in a slight increase in mean migration speed by 9% to 0.36 μm/min compared to untreated controls (FIG. 2A). In contrast, standalone iEF treatment in the anti-parallel direction resulted in the mean migration speed to increase significantly by 46% to 0.48 μm/min compared to the untreated control condition (FIG. 2A).

Figure 2B:
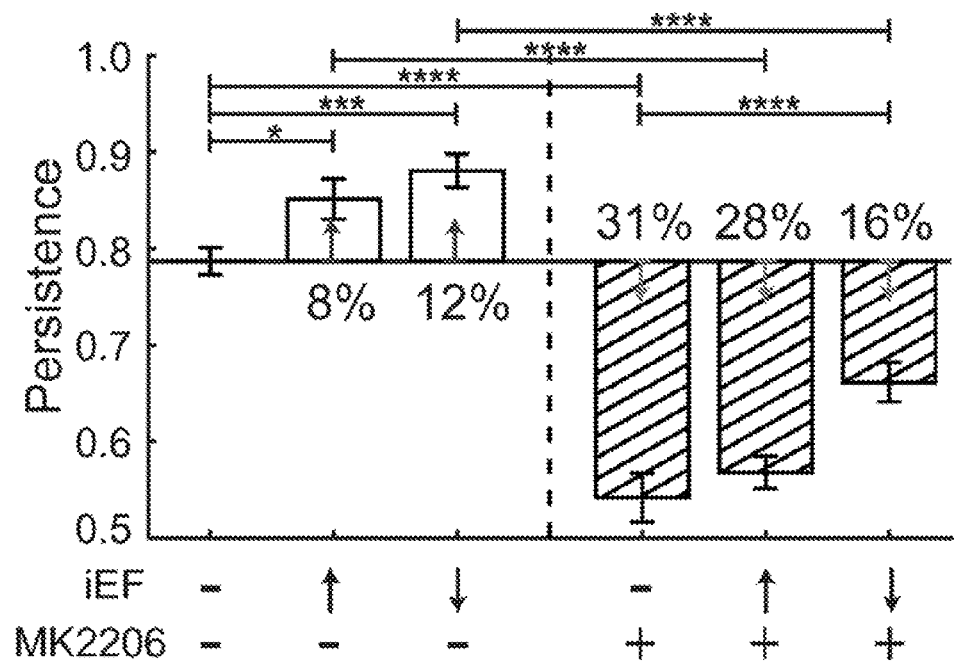
Figure 9:
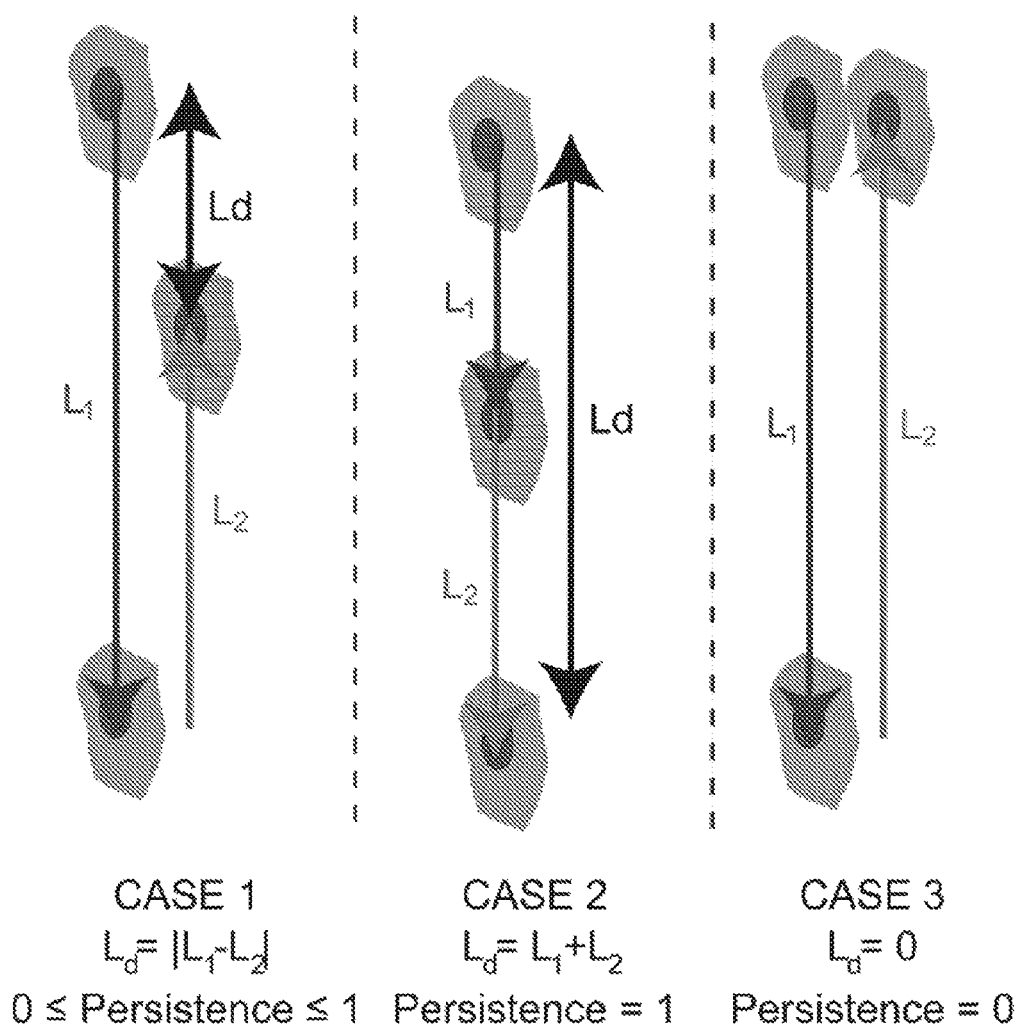
FIG. 9 shows quantitative metrics for cell motility enabled by MBDM Assay. The cell migrates a distance L1 in time t and then a distance L2 in the same time t. Therefore, the total distance travelled by cell during tracking is L1+L2 in time 2 t. Thus, mean speed is defined as the ratio of the total distance (in this case L1+L2) to the total time taken (2 t). Persistence is defined as the ability of a cell to maintain a single direction of motion. Mathematically, it is the ratio of the cell displacement to the total distance (L1+L2) travelled by the cell. Displacement is defined as the shortest distance (Ld) from the initial position to the final position of the cell. If the cell maintains a unidirectional motion then total distance is equal to displacement and therefore persistence equals one, whereas if the cell ends up at the same point from where it started then displacement is zero and hence persistence is zero.

Another important characteristic of cell motility is persistence or the ability to maintain a singular direction of migration (Maiuri P, et al. (2015) Cell 161 (2):374-386; Irimia D & Toner M (2009) Integr Biol (Camb). 1 (8-9):506-512). Established external regulators of persistence include chemotactic factors and mechanical cues such as the topography of the extracellular matrix (Petrie R J, et al. (2009) Nat Rev Mol Cell Biol. 10 (8):538), but the role of EFs in controlling this migration response is not well understood. To measure persistence, the ratio of the net displacement of a migrating cell from its starting point to the total distance traveled by the same cell within the same timeframe (FIG. 9) was examined in the MBDM assay. For MDA-MB-231 cells, standalone iEF treatment for both the parallel or anti-parallel directions significantly increased persistence compared to the untreated control condition (FIG. 2B). Thus, while the MDA-MB-231 cells selectively migrated faster to standalone iEFs applied in the anti-parallel direction (FIG. 2A), there was no significant difference between the persistence of these cells in the parallel and anti-parallel iEF cases (FIG. 2B).

Figure 8A:
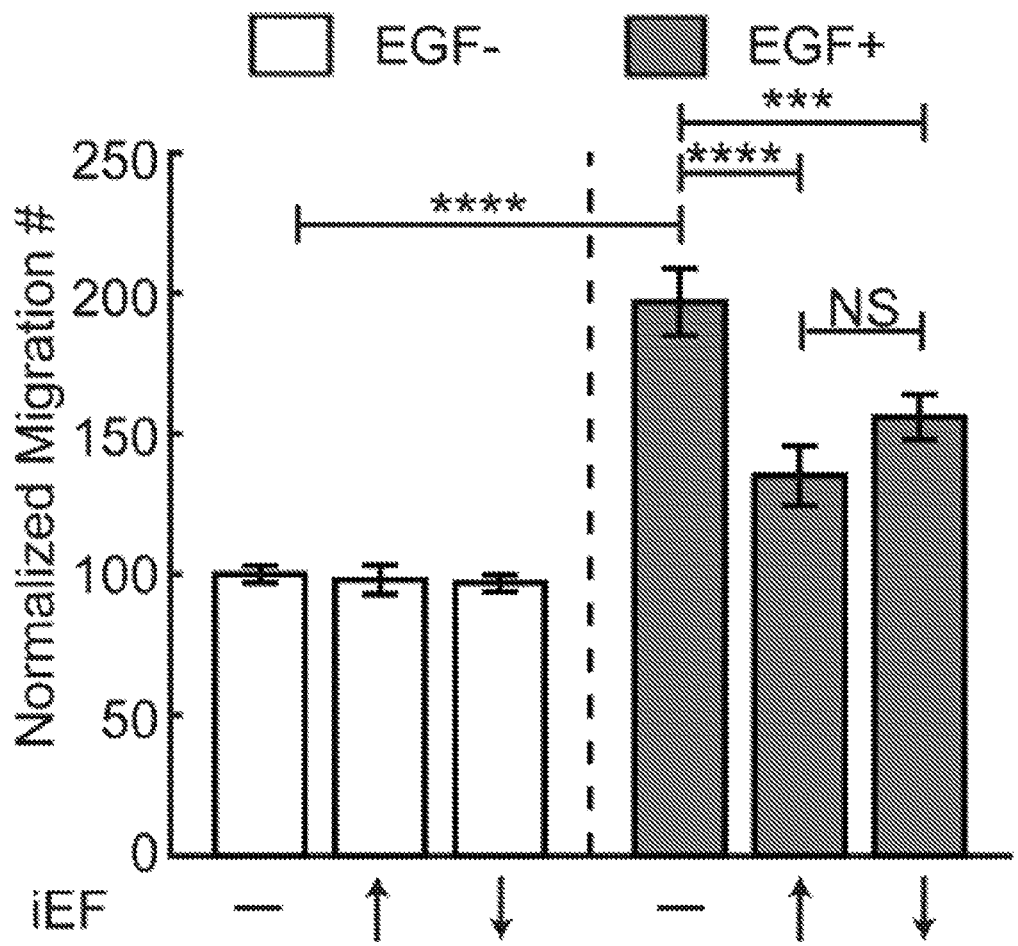
FIGS. 8A and 8B show modified transwell assay results.
Figure 8B:
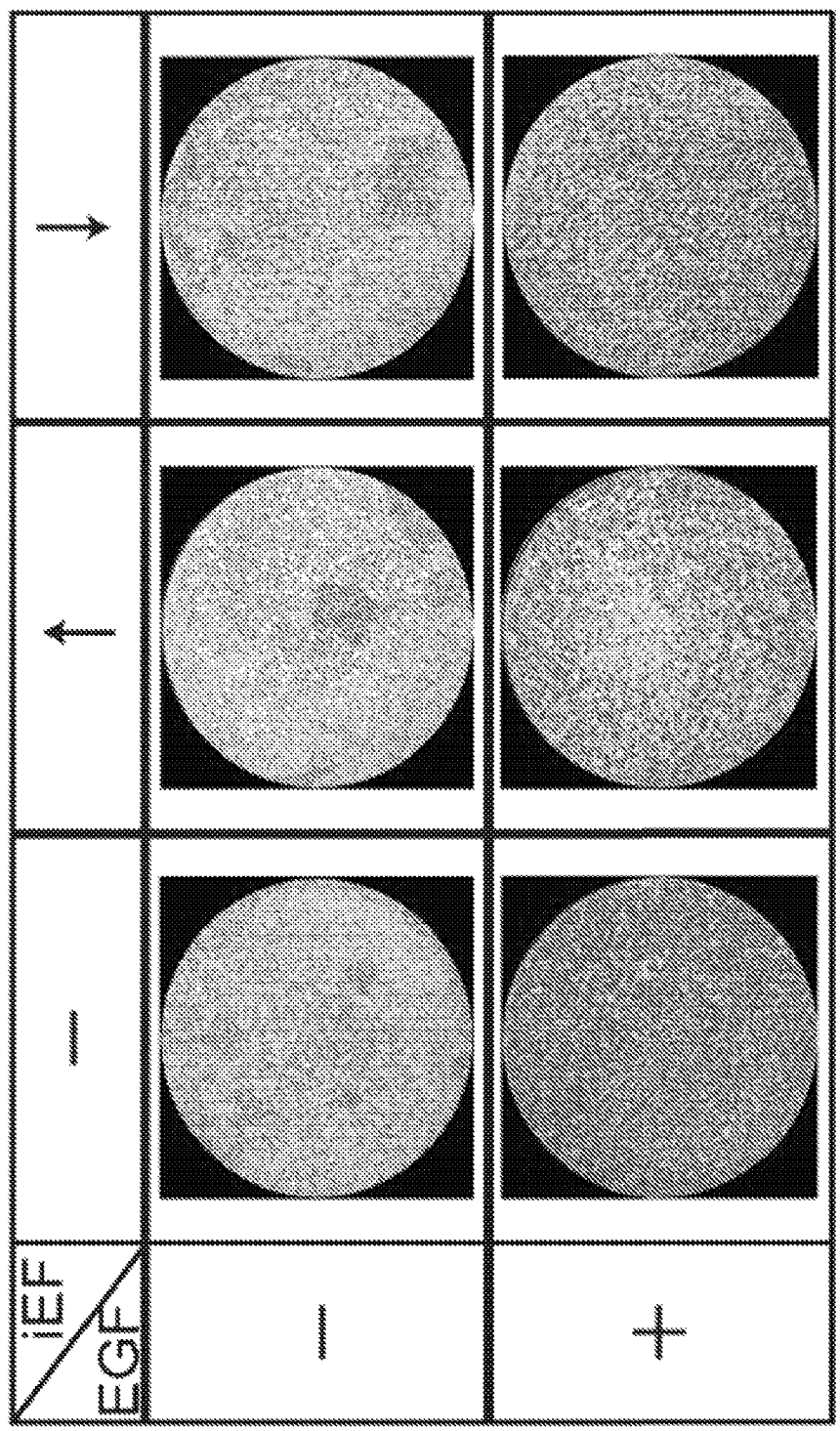

In addition to the MBDM assay, the modified transwell migration assay (Ahirwar D K, et al. (2015) Sci Rep 5:11005.) was used to determine the effects of standalone iEF treatment on number of cells migrated to complement the speed and persistence data obtained from the MBDM assay. iEF treatment alone had no significant effect (neither stimulatory nor inhibitory) on the total number of MDA-MB-231 cells that spontaneously migrated across the transwell membrane (~10 μm thick) compared to the untreated control (FIG. 8). These outcomes occurred for both anti-parallel and parallel directions of iEF application. Interestingly, these results for the MDA-MB-231 cells (FIG. 8A) were different from what had been previously reported for SCP2 cells, where iEFs significantly hindered transmigration only when applied parallel but not anti-parallel to the direction of migration (Ahirwar D K, et al. (2015) Sci Rep 5:11005). In summary, the MDA-MB-231 cells exhibited a directional response to standalone iEF treatment by preferentially migrating faster and with greater persistence when the iEFs were applied in the anti-parallel direction when compared to untreated controls.

Figure 10A:
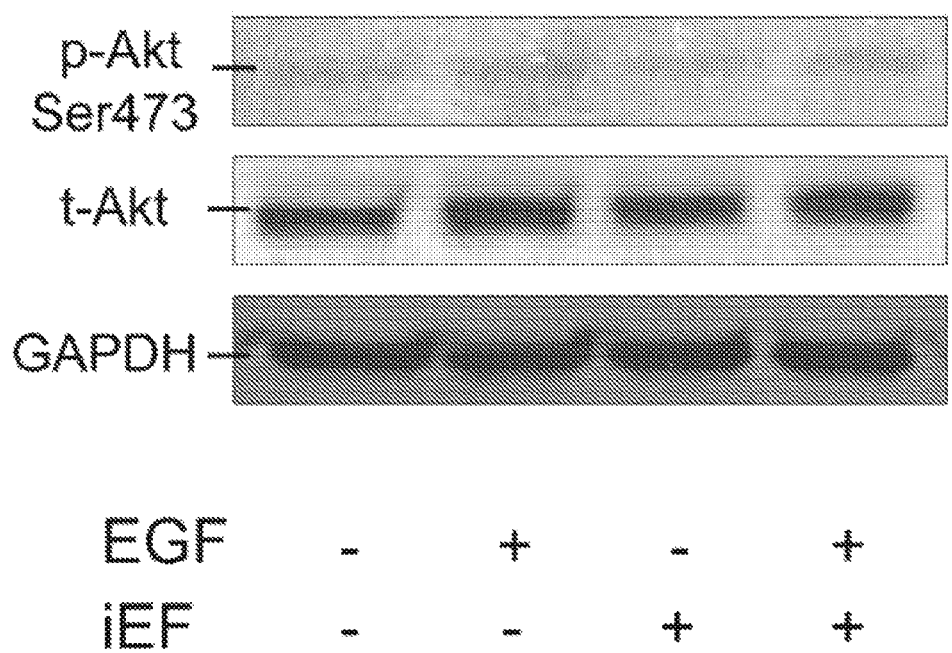
FIGS. 10A to 10C show effect of induced electric field treatment on levels of p-Akt and t-Akt levels in MDA-MB-231.
Figure 10B:
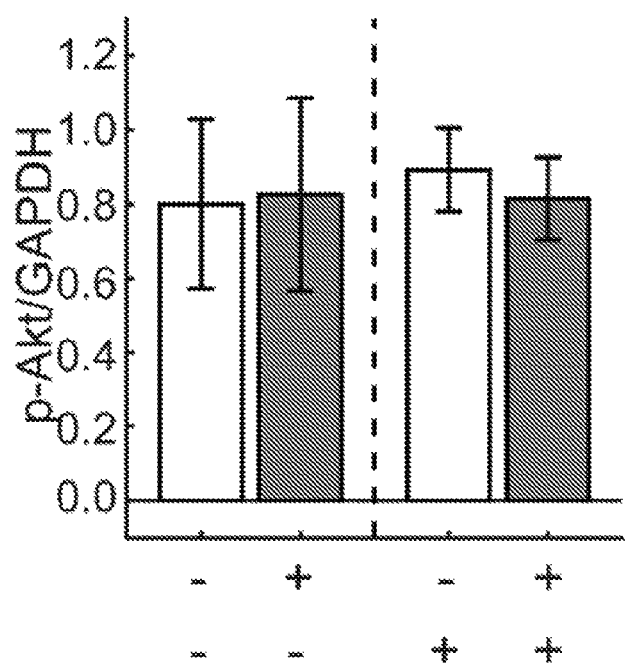
Figure 10C:
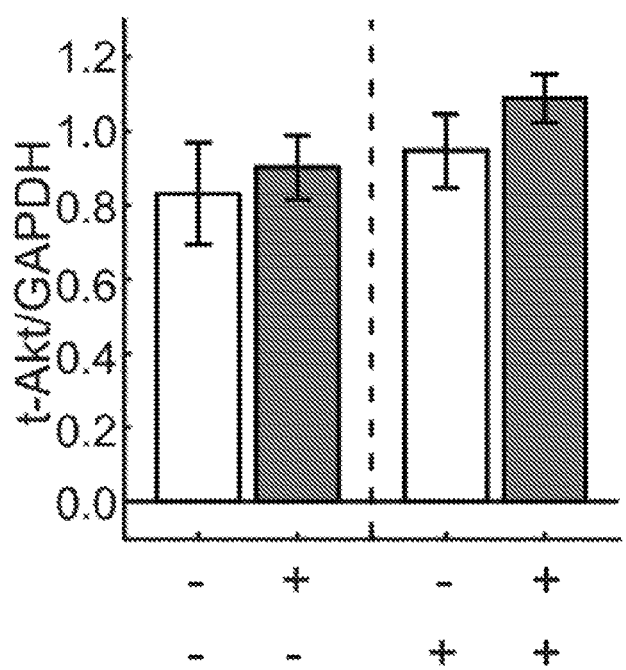

Directional Responses of Cell Motility to Induced Electric Fields is Mediated by Akt Signaling To further investigate the directional responses of the breast cancer cells to standalone iEF treatment, PI3K/Akt signaling was blocked next, which is an important pathway regulating the tumor promoting properties of cells, including motility (Vivanco I & Sawyers CL (2002) Nat Rev Cancer. 2 (7):489; Hennessy B T, et al. (2005) Nat Rev Drug Discov 4 (12):988-1004). Previous studies have shown that electrotaxis in response to current flow with dcEFs involving numerous cell types, including breast cancer, is PI3K/Akt-dependent (Zhao M, et al. (2006) Nature 442 (7101):457; Pu J, et al. (2007) J Cell Sci 120 (Pt 19):3395-3403). Therefore, it was hypothesized that the PI3K/Akt pathway is also involved with iEF-mediated electrotaxis of breast cancer cells. To inhibit this pathway, the Akt inhibitor MK2206 (2.5 μM) was used which inhibits phosphorylation of Akt-1, -2, and -3 that is downstream of the PI3K signaling (Hennessy B T, et al. (2005) Nat Rev Drug Discov 4 (12):988-1004; Cantley L C (2002) Science 296 (5573):1655-1657; Luo J, et al. (2003) Cancer Cell 4 (4):257-262). Surprisingly, application of MK2206 alone slightly increased the mean migration speeds of the MDA-MB-231 cells by 9% compared to untreated controls (FIG. 2A). Moreover, co-application of MK2206 with iEFs in both the parallel or anti-parallel directions resulted in a comparable modest decrease in the average migration speed of these cells compared to untreated controls (FIG. 2A). Therefore, the preference of the MDA-MB-231 cells to migrate faster in response to standalone anti-parallel iEFs versus parallel iEFs was completely abrogated when Akt was inhibited (FIG. 2A). The effects of Akt inhibition on persistence was also assessed. MK2206 treatment alone significantly reduced the persistence of the MDA-MB-231 cells by 31% (FIG. 2B) compared to untreated controls. However, co-application of MK2206 with iEFs in the anti-parallel, but not the parallel direction, significantly increased the persistence of these cells compared to MK2206 treatment alone (FIG. 2B) but remained significantly below untreated controls. Thus, unlike the effect on average migration speed where Akt inhibition abrogated the directional response to iEFs in MDA-MB-231 cells (FIG. 2A), inhibition of Akt promoted a directional response of MDA-MB-231 persistence to iEFs (FIG. 2B). Also explored was whether iEFs were altering the levels of Akt phosphorylation and/or total Akt levels of the MDA-MB-231 cells. Western blot data showed iEFs had no effect on Akt phosphorylation and total Akt levels (FIG. 10).

Figure 3A:
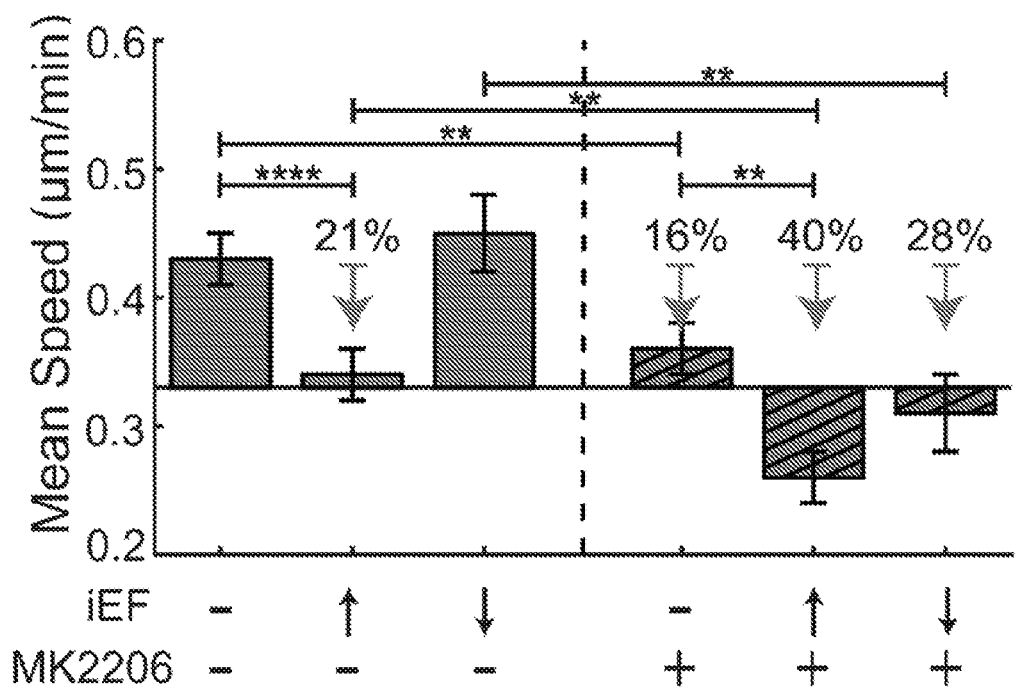
FIGS. 3A and 3B show iEF treatment decreases the motility of breast cancer cells migrating under EGF gradients.

Induced Electric Fields Potently Hinder EGF-Stimulated Breast Cancer Cell Motility Once establishing the effects of standalone iEF treatment on migration speed and persistence, next assessed was the role of iEFs in modulating these motility responses promoted by the pleiotropic signaling molecule EGF. Physiologically, breast cancer metastasis is often promoted by biomolecular gradients of EGF (Condeelis J & Segall J E (2003) Nat Rev Cancer 3 (12):921-930). Furthermore, its cognate receptor EGFR is commonly over-expressed in breast cancer cells and is often correlated with poor prognosis (Liu Y, et al. (2010) J Exp Clin Cancer Res 29 (1):16). In response to a stable EGF gradient (FIG. 11), as expected, the mean migration speeds of the MDA-MB-231 cells increased significantly compared to untreated controls (FIG. 3A). Interestingly, when iEFs were applied parallel to the direction of EGF-gradient promoted motility, the migration speeds of the MDA-MB-231 cells decreased significantly by 25% and returned to the level of their untreated control (0.33 μm/min). In contrast, iEFs applied anti-parallel to the direction of EGF-gradient promoted migration had no observable effect. Therefore, the mean speeds of MDA-MB-231 cells migrating in response to an EGF-gradient exhibited a directional response to iEFs. In terms of persistence, the MDA-MB-231 cells (FIG. 3B) migrated with an average persistence of 0.84 under stable EGF-gradients, which represents a significant 6% increase compared to the untreated control conditions. iEF treatment (parallel or anti-parallel) had no observable effect on the persistence of these cells.

Similar to studies on the effects of standalone iEF treatment on cell motility (FIG. 8), the modified transwell migration assay was also used to assess the migration responses of EGF-stimulated cells to iEF treatment. As expected, EGF stimulation significantly promoted the transmigration of the MDA-MB-231 cells (FIG. 8) compared to untreated controls. Interestingly, iEF treatment potently hindered EGF-promoted migration of the MDA-MB-231 cells for both the anti-parallel and parallel directions. Collectively, the results from the MBDM and transwell migration assays demonstrate clearly the capacity of iEFs to selectively hinder the motility of breast cancer cells when migrating under the influence of EGF gradients.

Induced Electric Fields and Akt Inhibitor Synergistically Hindered EGF-Promoted Migration To further investigate the hindering effects of iEFs on EGF-promoted migration of breast cancer cells, Akt signaling was next blocked, an important downstream effector of EGFR phosphorylation (Kolch W & Pitt A (2010) Nat Rev Cancer 10 (9):618-629; Nyati M K, et al. (2006) Nat Rev Cancer 6 (11):876-885). For MDA-MB-231 cells migrating under EGF-gradients, MK2206 treatment alone significantly reduced the mean migration speeds by 16% (from 0.43 μm/min to 0.36 μm/min) and returned values near to control levels (FIG. 3A). However, co-application of MK2206 with iEFs further reduced the mean migration speed of the MDA-MB-231 cells by 40% and 28% below EGF controls when applied in the parallel and anti-parallel directions respectively. Both treatments brought cell speeds below the untreated control level (0.26 μm/min and 0.31 μm/min respectively) with the parallel direction resulting in the slowest migration speed observed. Similar to the non-EGF treated case, these results show that the directional cellular response is Akt-dependent. Additionally, these results demonstrate that iEFs can work synergistically with MK2206 to reduce cell speeds below treatment with MK2206 or iEFs alone.

Figure 3B:
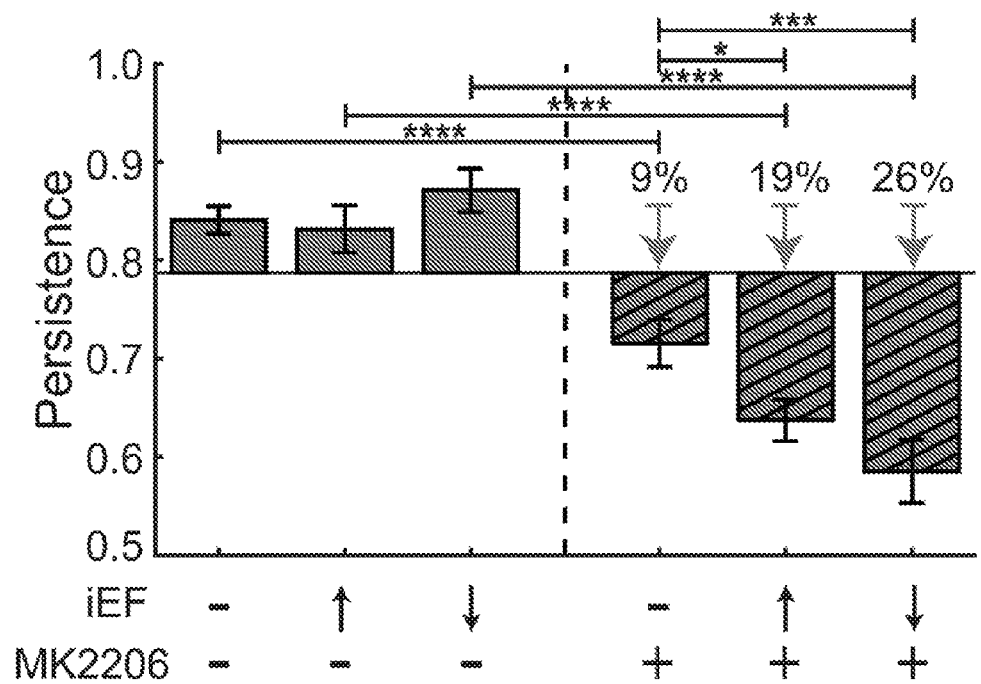

In terms of persistence, MK2206 alone significantly reduced levels 9% below the EGF-gradient conditions, falling below the average in the untreated case (FIG. 3B). Similar to cell speeds, combined treatment with MK2206 and iEFs further reduced the persistence of MDA-MB-231 regardless of direction. The parallel and anti-parallel directed iEFs brought the persistence level down 19% and 26% from the EGF control.

Interestingly, iEFs had no effect on levels of Akt phosphorylation or total Akt on EGF-treated MDA-MB-231 cells (FIG. 10). Therefore, iEFs do not appear to modulate migration speeds of EGF-treated MDA-MB-231 cells by directly interacting with Akt. Moreover, the observation that migration speeds and persistence of MDA-MB-231 cells under EGF-gradients are suppressed below control levels upon co-application of MK2206 and iEFs could have two possible explanations. Either iEFs increase the efficacy of MK2206 or iEFs and the MK2206 act concurrently along two independent pathways to suppress the motility potential of MDA-MB-231 migration under EGF-gradients.

Induced Electric Fields Alter the Distribution on F-Actin in Migrating Breast Cancer Cells A critical component to the cell polarity machinery is cytoskeletal F-actin whose polymerization plays a very important role in membrane extension (lamellipodia/pseudopodia/filopodia), formation of cell-substrate attachments, contractile force and traction, and release of attachments (Friedl P & Gilmour D (2009) Nat Rev Mol Cell Biol 10 (7):445-457). iEFs have recently been shown to significantly alter the distribution of F-actin in SCP2 breast cancer cells (Ahirwar D K, et al. (2015) Sci Rep 5:11005). This section reports on the effects of iEFs on the distribution of F-actin in cells migrating along the microtracks of the MBDM assay. To quantify the distribution of F-Actin, a quantity referred to herein as the polarization ratio (PR) was introduced, which has values between 0 and 1. A PR of 0 indicates that there is no localization of F-actin at the leading and/or trailing edges of the cells, while a PR of 1 indicates there is a very high concentration of F-actin localization at the leading and/or trailing edges of migrating cells in the microchannels of the MDBM assay.

Figure 4A:
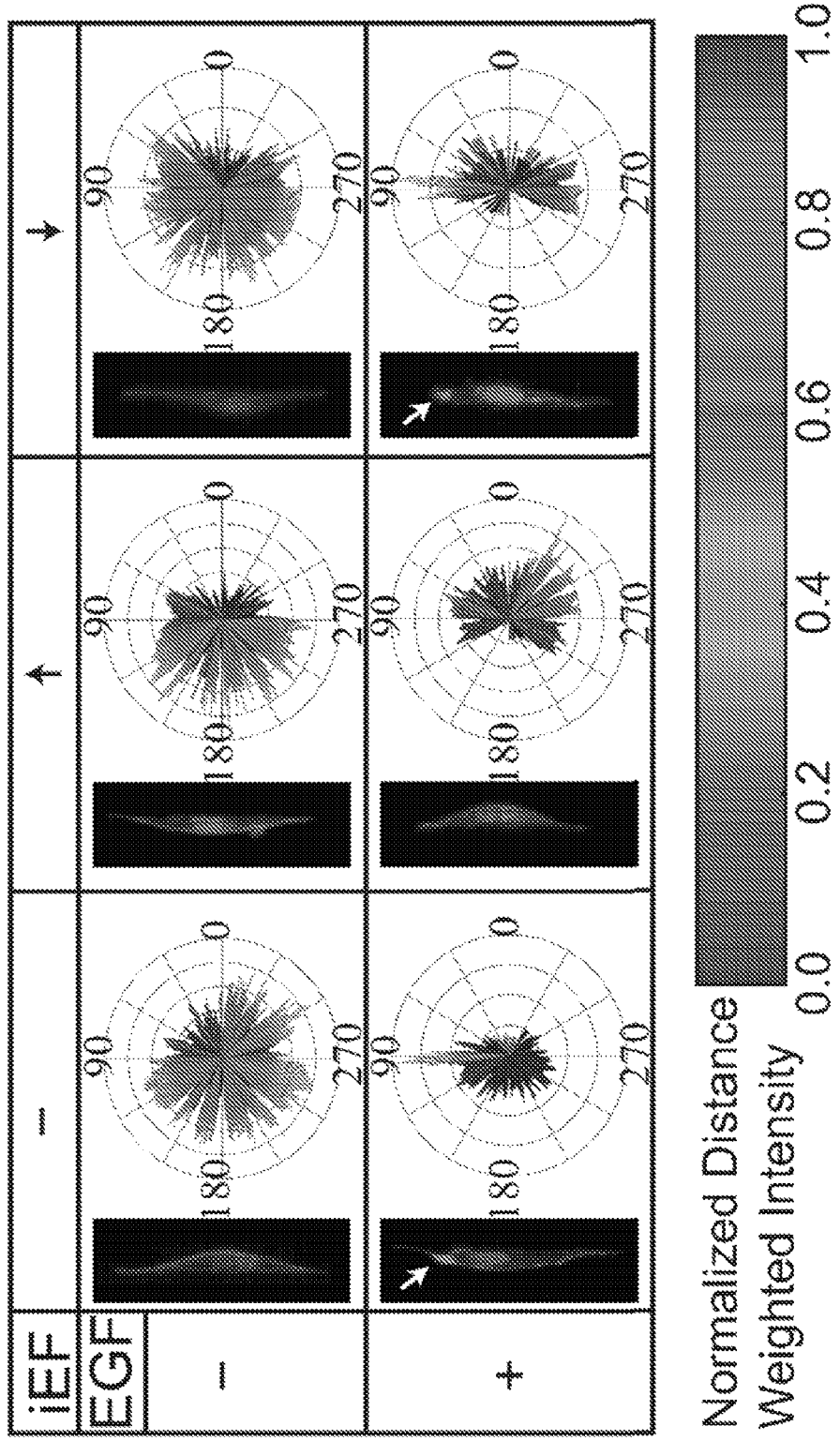
FIGS. 4A and 4B show iEF treatment inhibits EGF-promoted actin aggregation at the leading edge of migrating cells.
Figure 4B:
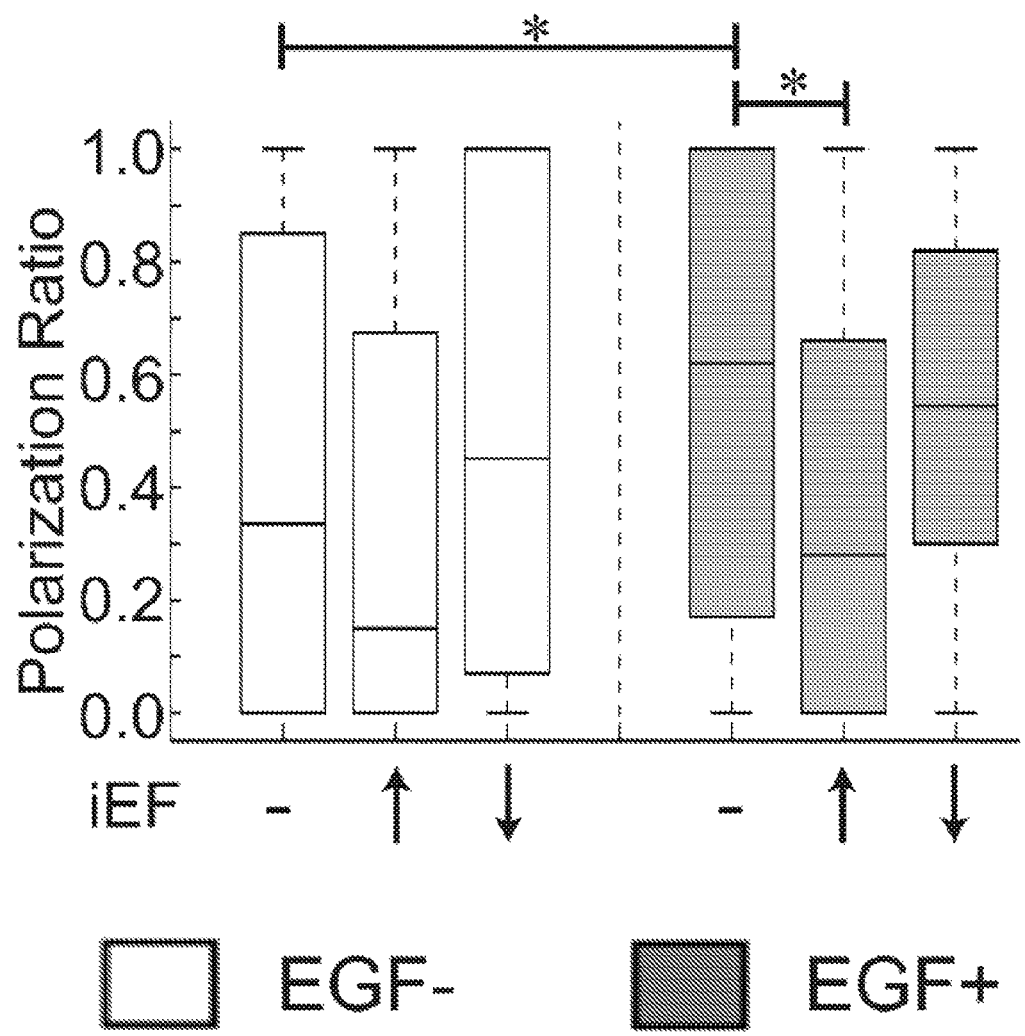

For MDA-MB-231 cells (FIGS. 4A, 4B), the center of the distribution of PR for cells migrating in the absence of EGF and iEFs was found to be 0.34. When iEFs were applied parallel to the direction of migration and in the absence of EGF, centers of the PR distribution decreased to 0.15. However, it is important to point out that this is not a significant change compared to the control case; moreover, the speeds were found to be comparable to those in the control case. When iEFs were applied anti-parallel to the direction of migration and in the absence of EGF, the center of the PR distribution increased to 0.45 but again this change was not statistically significant. Although this upward shift was statistically insignificant, the increase mirrored the higher migration speeds measured for this case as compared to the control condition.

The center of the PR distribution for cells migrating under EGF-gradients in the absence of iEFs changed to 0.62, implying that there were a higher proportion of cells with F-actin localization at the leading/trailing edges compared to the case where EGF and iEFs are absent. In the presence of EGF gradients, iEFs applied parallel to the direction of migration decreased the PR center to 0.28. This represents a statistically significant decrease of ~55% compared to the case with EGF while iEFs applied anti-parallel to the direction of migration resulted in no significant changes to the PR center.

In summary, actin distribution under the action of iEFs agree with observed changes in the mean migration speeds of the MDA-MB-231 cells. Consistent with what has been reported previously for SCP2 cells (Ahirwar D K, et al. (2015) Sci Rep 5:11005), the distribution of cytoplasmic F-actin and suppression of filopodia in the presence of iEF is also observed in the present experiments even with a different cell line.

Induced Electric Fields Have No Effect on Focal Adhesion Kinase Expression

Figure 12A:
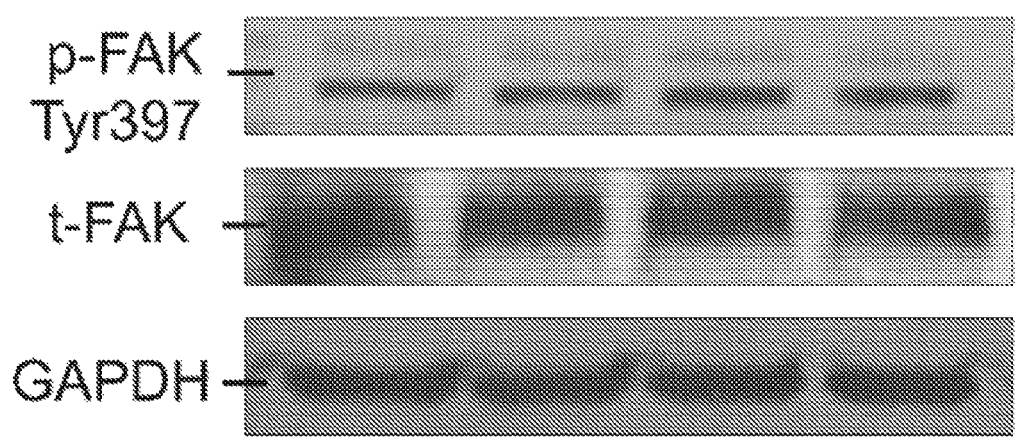
FIGS. 12A to 12C show effect of iEF treatment on levels of p-FAK and t-FAK levels in in MDA-MB-231.
Figure 12B:
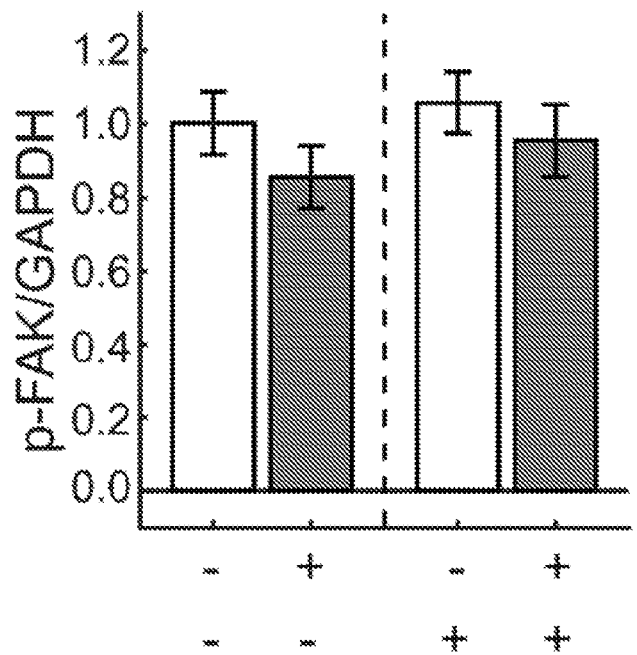
Figure 12C:
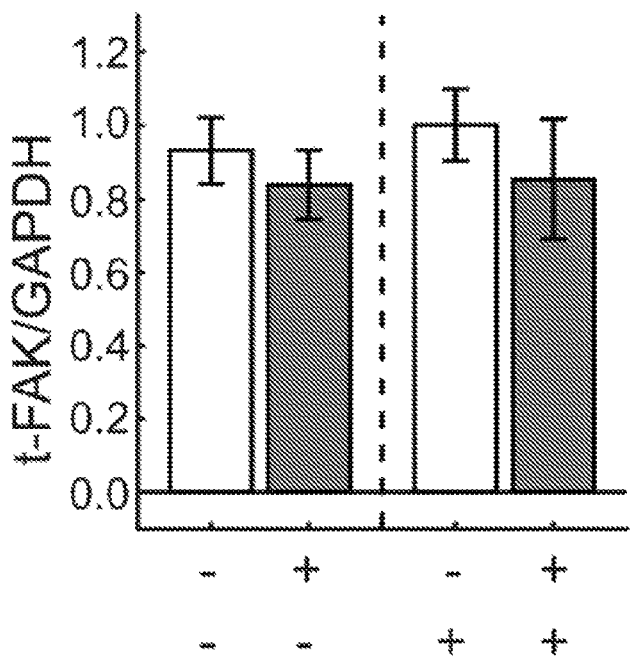

Focal adhesion kinase (FAK), a non-receptor protein kinase, is a potent driver of both the tumor growth and metastasis and is commonly overexpressed in invasive breast carcinoma (Sulzmaier F J, et al. (2014) Nat Rev Cancer. 14 (9):598). Talin and cortactin, FAK-associated proteins, are known to bind to actin thereby connecting focal adhesions to changes in actin dynamics (Mitra S K, et al. (2005) Nat Rev Mol Cell Biol. 6 (1):56). FAK has been found to localize to sites of integrin-EGFR clusters on EGF treatment in order to regulate signaling, thereby regulating cell motility of DA2 fibroblasts (Sieg D J, et al. (2000) Nat Cell Biol. 2 (5):249). Ability of FAK to localize with the integrin-EGFR cluster and regulate signaling make it a "receptor proximal regulatory protein". For EGF to stimulate integrin-mediated motility of DA2 cells, both phosphorylation of FAK at Tyr397 and actin cytoskeleton integrity is necessary (Sieg D J, et al. (2000) Nat Cell Biol. 2 (5):249). Integrins are also known to recruit FAK that in turn associates with Rho GTPases. The Rho GTPases (Rho, Rac, Cdc42) act as regulatory convergence node that dictates cytoskeleton and adhesion assembly and organization (Parsons J T, et al. (2010) Nat Rev Mol Cell Biol. 11 (9):633). Therefore, western blot analysis was used to understand if iEF treatment was changing activation and/or expression of FAK that could then be linked to changes observed in actin distribution and cell motility on treatment with iEFs. iEFs had no effect on the phosphorylation or total levels of FAK in MDA-MB-231 cells (FIG. 12). In summary, all changes observed in actin distribution, cell migration speeds, and persistence for iEF-treated MDA-MB-231 cells were not regulated through FAK. Since cell migration inherently involves F-actin and EGF induced motility involves EGFR, the effects of iEF on EGFR regulation was next explored.

Induced Electric Field Treatment Downregulates EGFR Activation

Figure 5A:
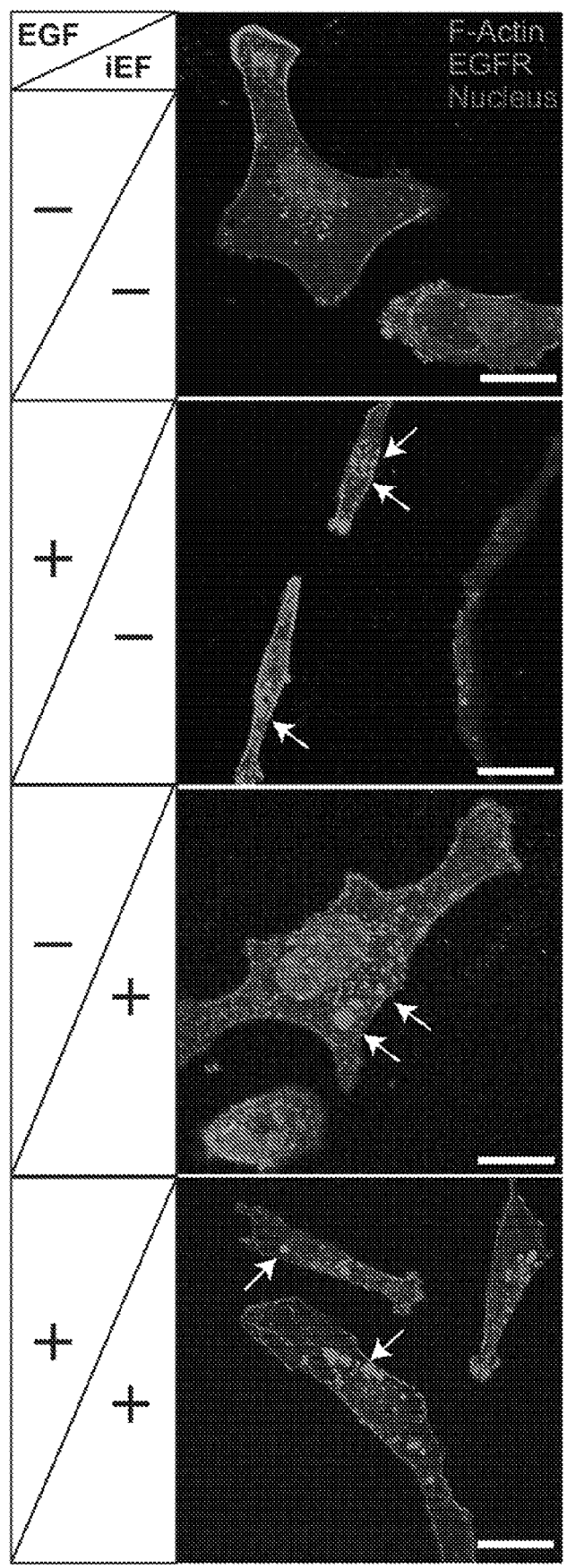
FIGS. 5A to 5E show iEF treatment promotes EGFR aggregation but downregulates EGFR-phosphorylation.

To determine whether iEFs conferred a direct effect on EGFR activation and to explore possible mechanisms that may be controlling the cell motility response to iEF treatment, the spatial distribution of EGFR, its expression, and its phosphorylation was examined. EGFR is a receptor tyrosine kinase and its signaling is activated by ligand-induced dimerization or oligomerization (Needham S R, et al. (2016) Nat Commun. 7:13307). Further, receptor clustering or aggregation has been shown to result in EGFR activation (Ichinose J, et al. (2004) Biochem Biophys Res Commun 324 (3):1143-1149; Sako Y, et al. (2000) Nat Cell Biol 2 (3):168-172). Therefore, the effects of iEF treatments on spatial EGFR expression were analyzed using immunofluorescence staining. With MDA-MB-231 cells, EGFR was found to be uniformly expressed under untreated control conditions (FIG. 5A). Upon standalone iEF treatment, there were striking changes in the spatial distribution of EGFR through the formation of EGFR aggregates and clusters (FIG. 5A). Similarly, treatment of the MDA-MB-231 cells with only EGF, also resulted in some clustering of EGFR (FIG. 5A), but to a lesser degree than with iEF treatment alone. Further, iEF treatment in presence of EGF did not alter the EGFR clustering previously observed with iEF treatment alone; EGFR continued to display clustered states for this condition (FIG. 5A). Therefore, iEFs resulted in clustering of EGFR independent of EGF treatment. To understand if this level of clustering induced receptor activation or deactivation, we used western blot analysis.

Figure 5B:
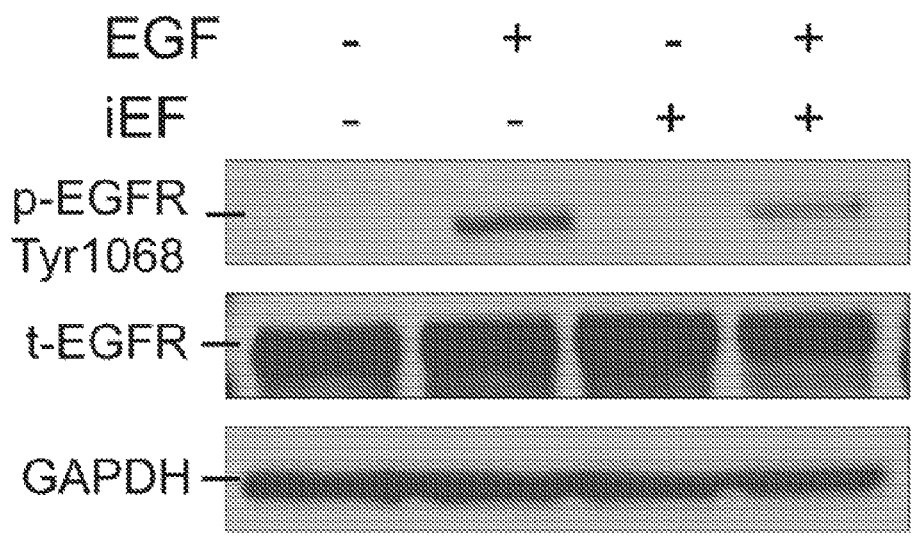
Figure 5C:
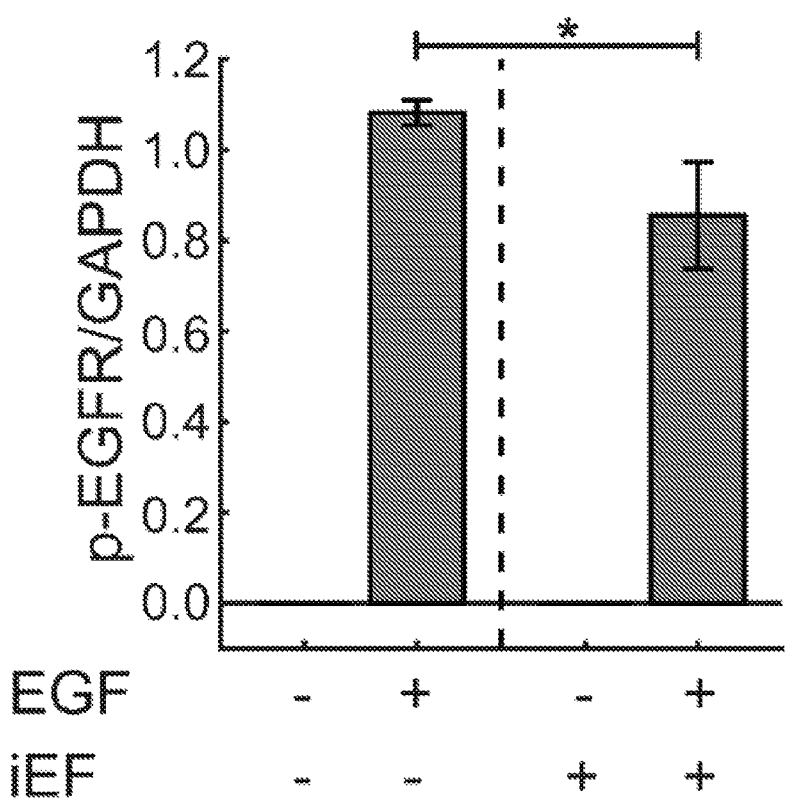
Figure 5D:
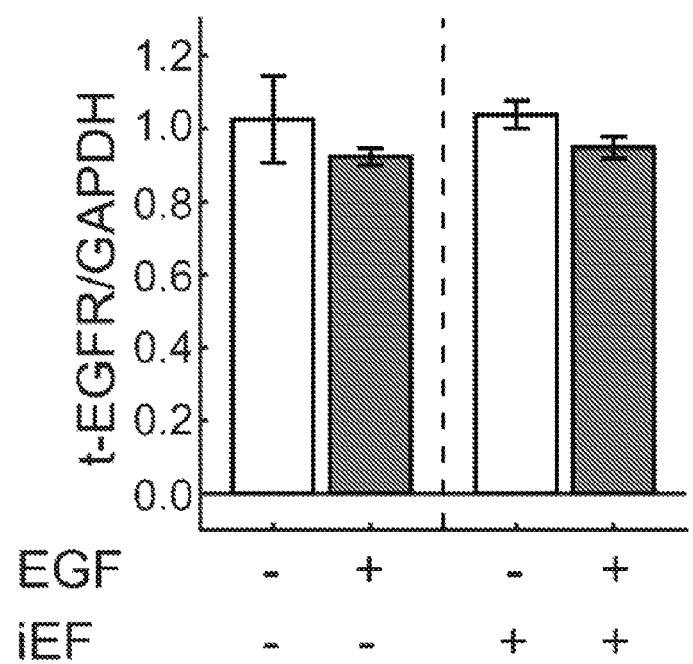
Figure 5E:
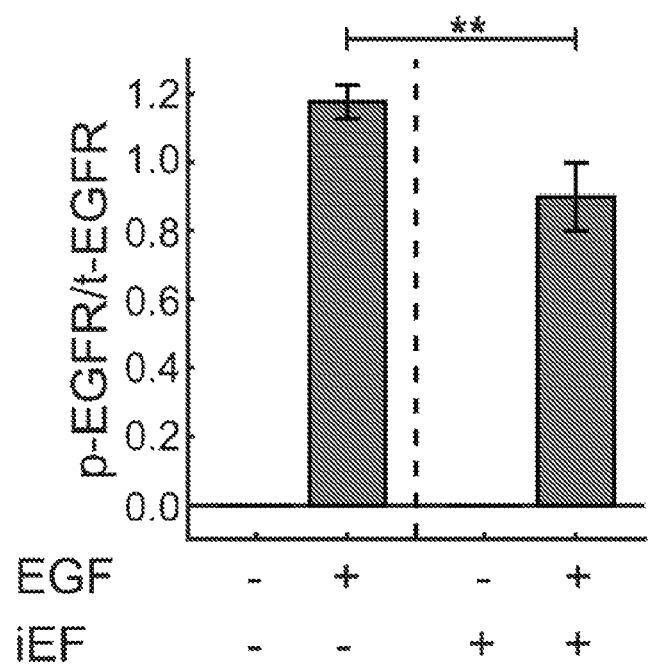

In the MDA-MB-231 cells, negligible phosphorylation of EGFR was observed at the Tyr-1068 site for the control case (FIG. 5B). iEF treatment in the absence of EGF did not result in produce any significant phosphorylated EGFR (p-EGFR) (FIG. 5B). Therefore, the EGFR clustering observed in the absence of EGF and upon iEF treatment did not result in auto-phosphorylation and hence EGFR continued to remain in its inactive state. As expected, EGF treatment in absence of iEFs resulted in EGFR phosphorylation (FIG. 5B). Moreover, the clustering observed in presence of EGF and EGFR activation result is in line with other previous reported studies (Ichinose J, et al. (2004) Biochem Biophys Res Commun 324 (3):1143-1149; Sako Y, et al. (2000) Nat Cell Biol 2 (3):168-172). In contrast, iEF treatment on EGF treated MDA-MB-231 cells, significantly downregulated phosphorylation of EGFR by ~21% (FIG. 5B). Therefore, the EGF induced activation of EGFR was downregulated by iEF treatment despite continued receptor clustering. No changes in the expression levels of total EGFR (t-EGFR) were observed for any of the above conditions (FIG. 5D). Consistent with the above results, the ratio of p-EGFR to t-EGFR followed the same trend as p-EGFR where iEF treatment on EGF-stimulated MDA-MB-231 cells significantly downregulated activated EGFR to total EGFR levels by ~24% when compared to EGF-stimulated cells in the absence of iEFs (FIG. 5E). Therefore, these results show that iEFs hinder EGF-promoted motility of MDA-MB-231 cells by downregulating EGFR phosphorylation.

Induced Electric Field Treatment Downregulates SDH Activity in the Presence of EGF Both phosphorylation of EGFR and actin treadmilling require constant supply of adenosine triphosphate (ATP) (Pantaloni D, et al. (2001) Science 292 (5521):1502-1506). ATP-hydrolysis on G-actin destabilizes actin and results in initiation of actin treadmilling. On de-polymerization (F-actin to G-actin), ATP is not resynthesized but the actin replaces the bound ADP with ATP from the medium (Korn E D, et al. (1987) Science 238 (4827):638-644; Carlier M-F (1990) Adv Biophys. 26:51-73). Therefore, any actin redistribution, especially directed actin treadmilling to induce cell migration, requires a constant supply of ATP. Further, it has been previously shown that inhibition of AMP-activated protein kinase (a major metabolic regulator (Mihaylova M M & Shaw R J (2011) Nat Cell Biol. 13 (9):1016)) inhibited the growth of EGFR activated gliomas.

Figure 6A:
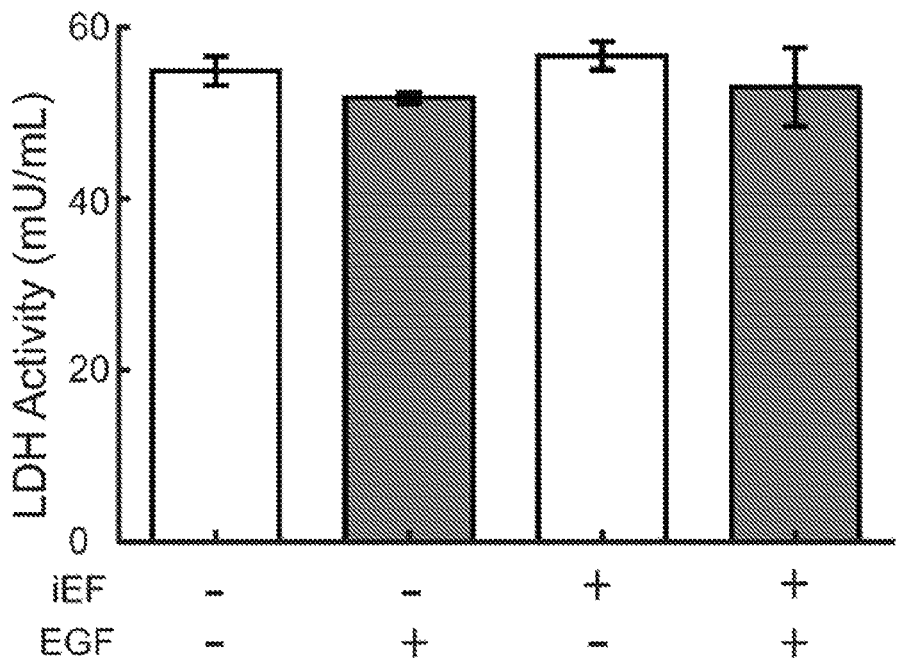
FIGS. 6A and 6B show iEF treatment has no effect on the enzymatic activity of LDH but significantly downregulates SDH activity on EGF-treated MDA-MB-231 cells.
Figure 6B:
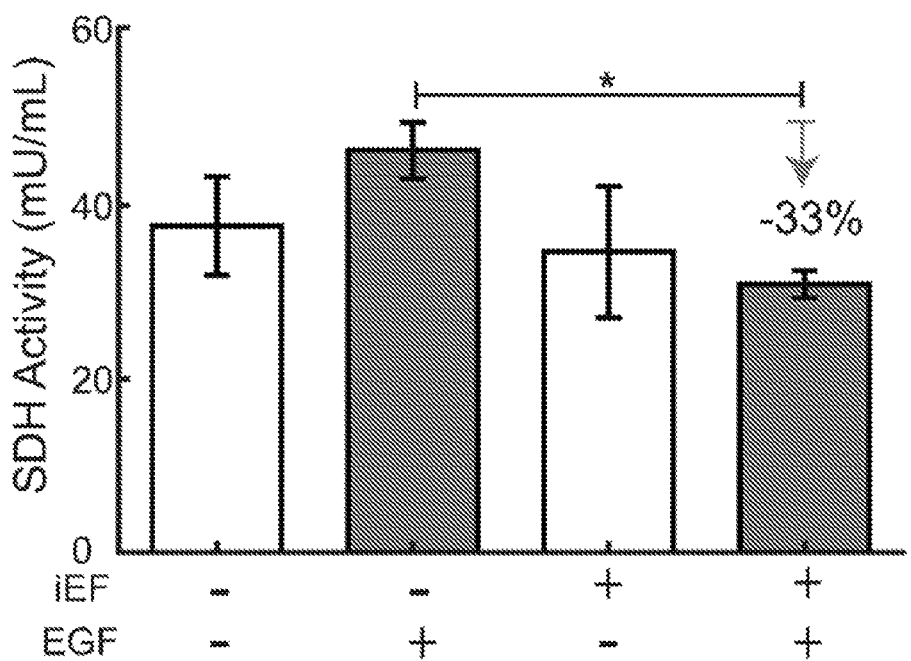
Figure 7A:
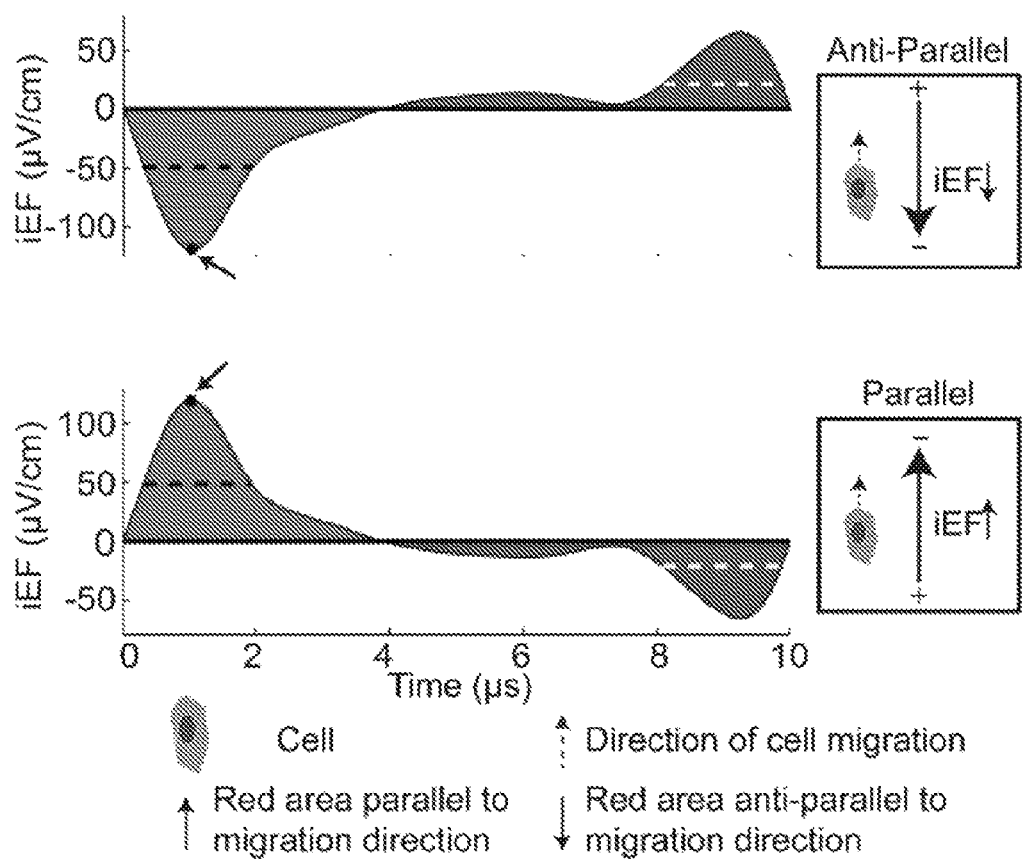
FIGS. 7A to 7C show characterization of the induced electric fields.
Figure 7B:
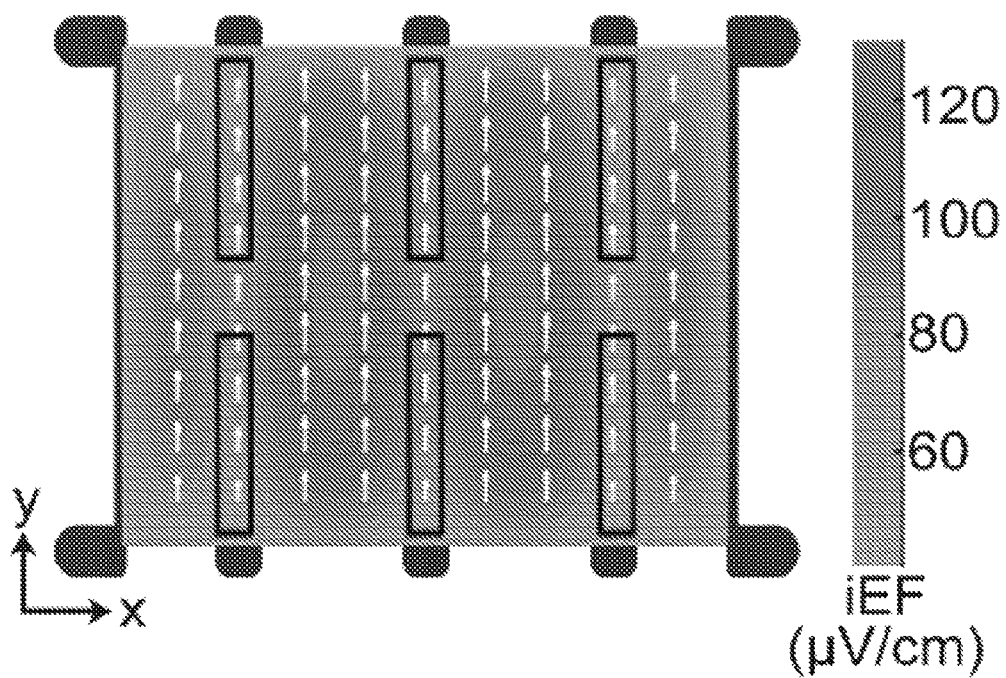
Figure 7C:
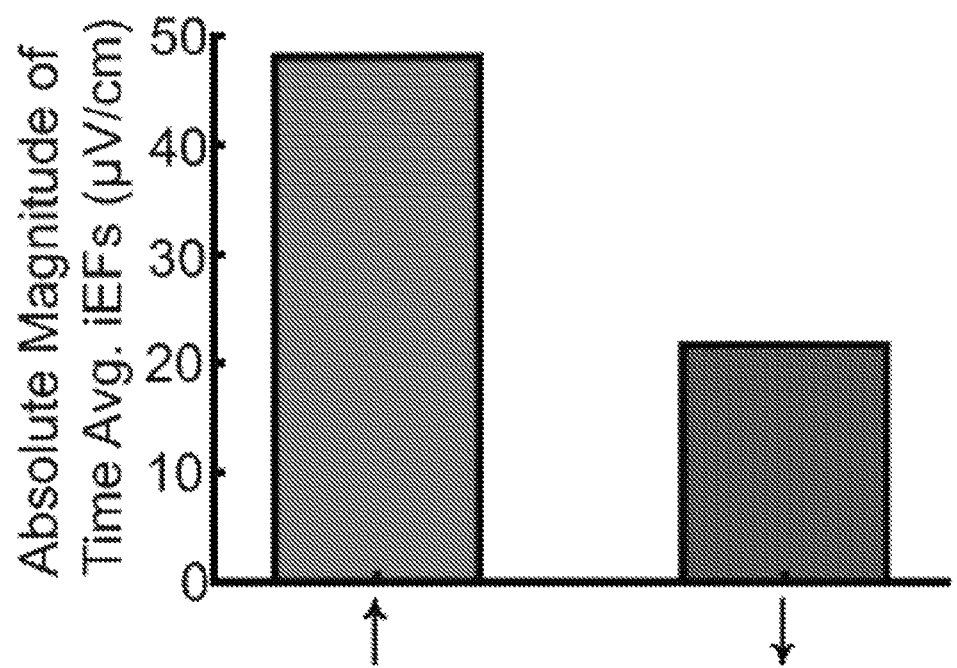

To investigate whether iEF has an effect on metabolic function of MDA-MB-231 cells, the activity levels of lactate dehydrogenase (LDH) and succinate dehydrogenase (SDH) were examined. LDH is an enzyme that catalyzes the interconversion of pyruvate to lactate as part of the glycolysis chain (Pelicano H, et al. (2006) Oncogene 25 (34): 4633). SDH is an enzyme within Complex II of the mitochondria that is utilized in both the tricarboxylic acid (TCA) cycle as well as oxidative phosphorylation (OXPHOS) (Gottlieb E & Tomlinson IP (2005) Nat Rev Cancer. 5 (11):857). As part of the TCA cycle, SDH catalyzes the oxidation of succinate to fumarate, and as part of OXPHOS, SDH transfers two electrons from flavin adenine dinucleotide into the electron transport chain (Gottlieb E & Tomlinson IP (2005) Nat Rev Cancer. 5 (11):857). To determine whether LDH or SDH activity levels were changing, colorimetric kinetic assays were employed. It was found that LDH activity levels were not significantly altered in the presence of EGF or iEF as compared to control (both <6% change from control, FIG. 6A). Additionally, combination treatment of EGF and iEF showed no significant changes from either the control case or EGF case. SDH activity increased by 23% in the case of EGF but was not significant (FIG. 6B). In both cases of iEF treatment (with and without EGF), there was no significant change in SDH activity as compared to the control case. There was however a significant 33.23% decrease in SDH activity in combination of EGF and iEF as compared to EGF treatment alone (FIG. 6B). These results show that while iEF is not affecting the basal level of metabolism, it appears to hinder increased production of ATP by OXPHOS in mitochondria when stimulated with EGF.

Characterization of Electric Fields Generated By the Helmholtz Coil

Figure 13A:
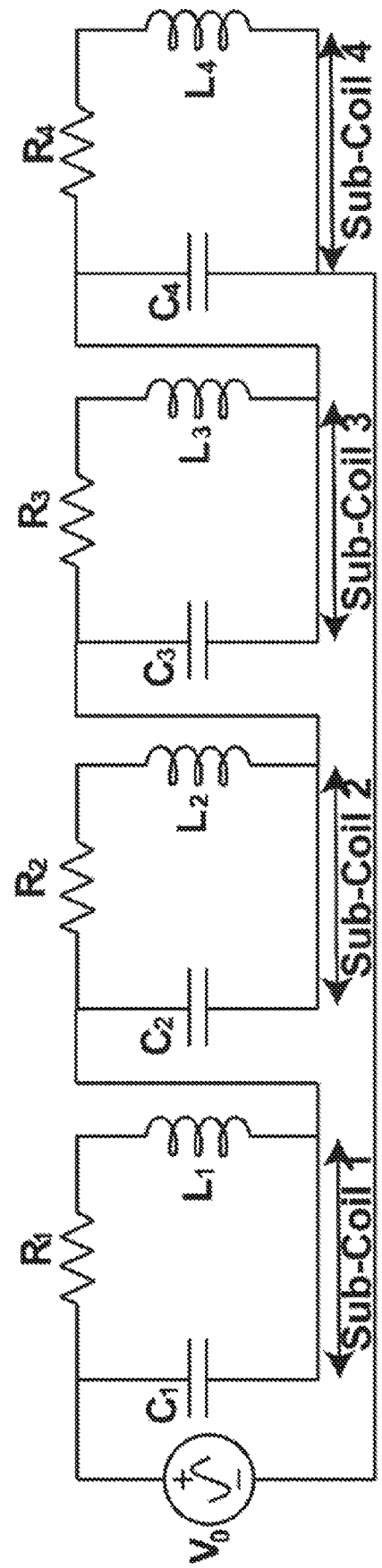
FIG. 13A shows circuit Element Model. Simplified circuit element model of Helmholtz coil used in experiments. The coil is composed of four similar coil segments in series. The first and fourth segments are identical, as are the second and third segments.
Figure 13B:
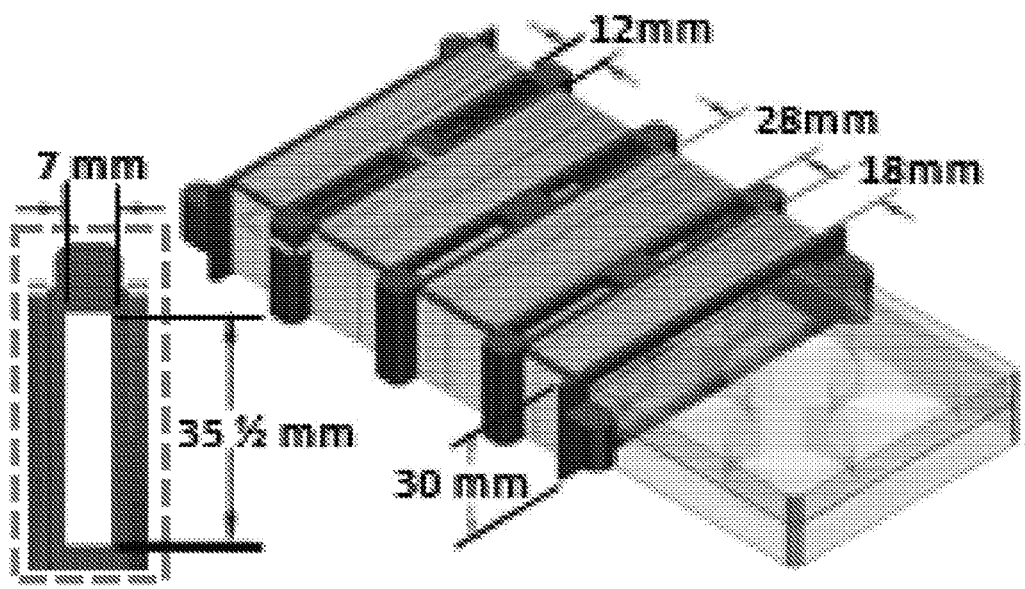
FIG. 13B shows an example Helmholtz Coil. Schematics indicating the dimensions of the coil and the microscope viewing windows.
Figure 14A:
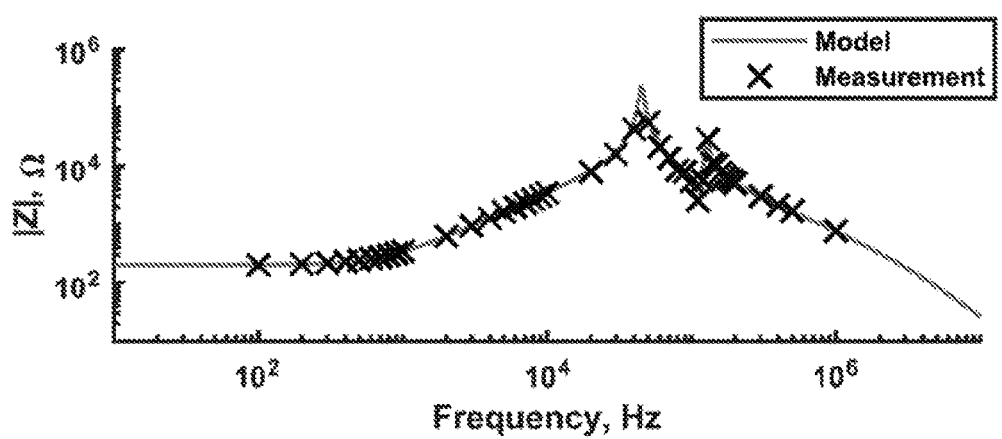
FIGS. 14A and 14B shows frequency response of a Helmholtz Coil.
Figure 14B:
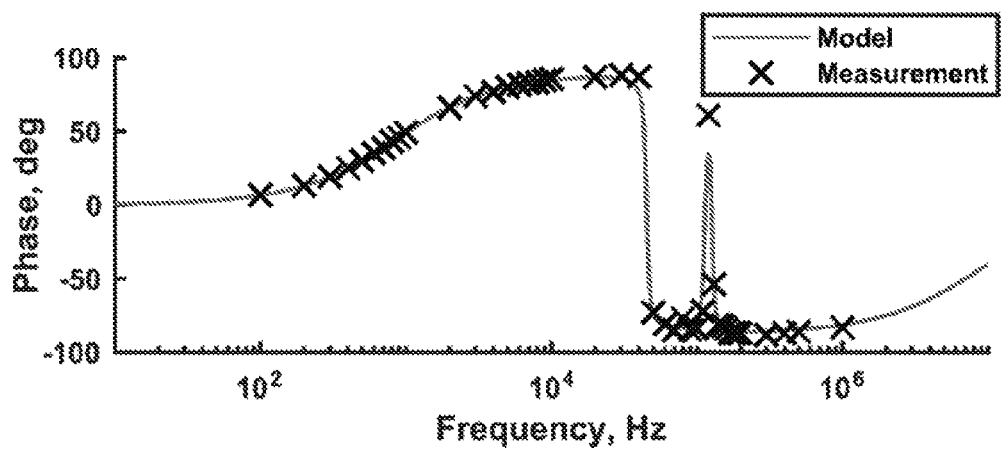

The Helmholtz coil used in some of the experiments reported in this paper comprises 4 segments. FIG. 13 shows a simplified circuit model of the Helmholtz coil showing these 4 segments, each comprising a resistance, capacitance, and inductance. The frequency response of the Helmholtz coil was determined by measuring the voltage drop across a 1000 sense resistor connected in series with the coil. A sine wave voltage waveform was then applied and the amplitude and phase of the signal across the resistor monitored. The impedance was inferred based on the applied potential and measured current through the resistor. The resonant frequencies of the inner and outer coil segments of the Helmholtz coil were determined from the two impedance peaks in the frequency response. Lump inductance and resistance were measured using an LCR meter (Keysight U17330). Values of inductance and resistance of each coil segment were adjusted assuming the total inductance and resistance of the coil is an aggregate of the individual inductances and resistances of each coil segment. To match the resonant frequency peaks, the capacitance of each coil segment was determined by the inferred inductance based on the relation: $f = 1/(2\pi\sqrt{LC})$. FIG. 14 shows a comparison of the circuit element model using the fit parameters with measured values of the frequency response of the coil.

Figure 15:
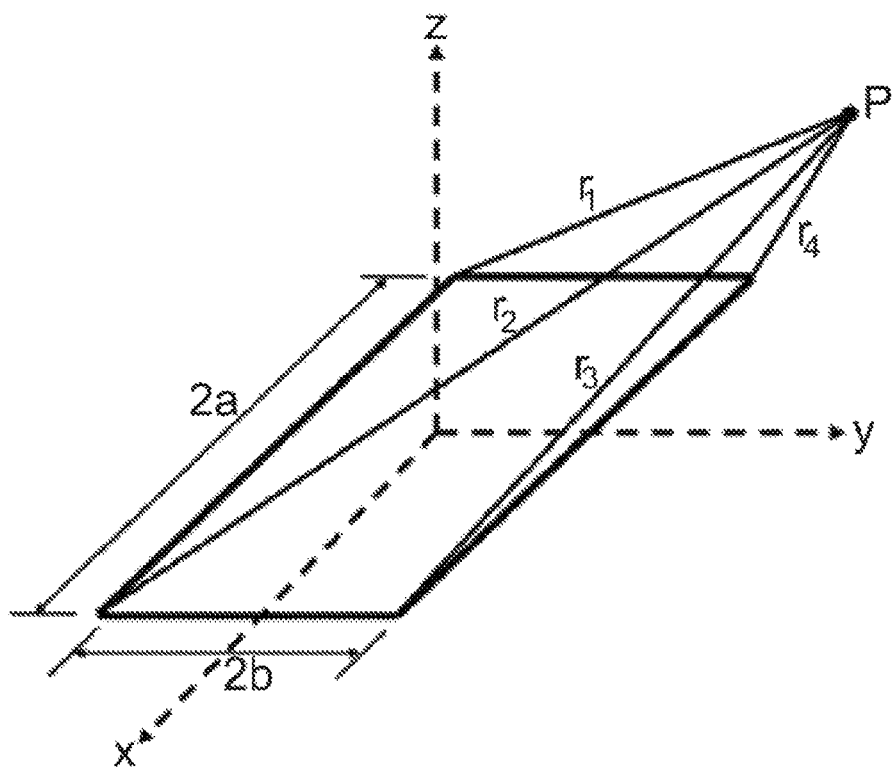
FIG. 15 shows geometry of a single rectangular loop of current used for calculating the vector potential $\vec{A}$ at point P(x,y,z) with respect to a coordinate system.

Closed form solutions for the vector potential $\vec{A}$ and magnetic induction $\vec{B}$ for a Helmholtz coil of rectangular cross section, are available in the literature (Misakian, M., (2000) J Res Natl Inst Stand Technol. 105 (4):557). The depiction of the various quantities appearing in the formulae given below is given in FIG. 15. The relevant expressions for the components of the vector potential $\vec{A}$, induced electric field $\vec{E}$, and magnetic induction $\vec{B}$ at a point P(x, y, z) are:

$$A_x = \frac{\mu_0 I}{4\pi} \ln\left[\frac{(r_1 + a + x)}{(r_2 - a + x)} \frac{(r_3 - a + x)}{(r_4 + a + x)}\right] \tag{S1}$$

$$A_y = \frac{\mu_0 I}{4\pi} \ln\left[\frac{(r_2 + b + y)}{(r_3 - b + y)} \frac{(r_4 - b + y)}{(r_1 + b + y)}\right] \tag{S2}$$

$$\vec{E} = -\frac{\partial \vec{A}}{\partial t} \tag{S3}$$

$$E_x = -\frac{dI}{dt} \frac{\mu_0}{4\pi} \ln\left[\frac{(r_1 + a + x)}{(r_2 - a + x)} \frac{(r_3 - a + x)}{(r_4 + a + x)}\right] \tag{S4}$$

$$E_y = -\frac{dI}{dt} \frac{\mu_0}{4\pi} \ln\left[\frac{(r_2 + b + y)}{(r_3 - b + y)} \frac{(r_4 - b + y)}{(r_1 + b + y)}\right] \tag{S5}$$

$$B_z = \frac{\mu_0 I}{4\pi} \sum_{n=1}^{4} \left[\frac{(-1)^n d_n}{r_n[r_n + (-1)^{n+1} C_n]} - \frac{C_n}{r_n[r_n + d_n]}\right] \tag{S6}$$

$$C_1 = -C_4 = a + x$$

$$C_2 = -C_3 = a - x$$

$$d_1 = d_2 = y + b$$

$$d_3 = d_4 = y - b$$

$$r_1 = \sqrt{(a+x)^2 + (y+b)^2 + z^2}$$

$$r_2 = \sqrt{(a-x)^2 + (y+b)^2 + z^2}$$

$$r_3 = \sqrt{(a-x)^2 + (y-b)^2 + z^2}$$

$$r_4 = \sqrt{(a+x)^2 + (y-b)^2 + z^2}$$

Figure 16A:
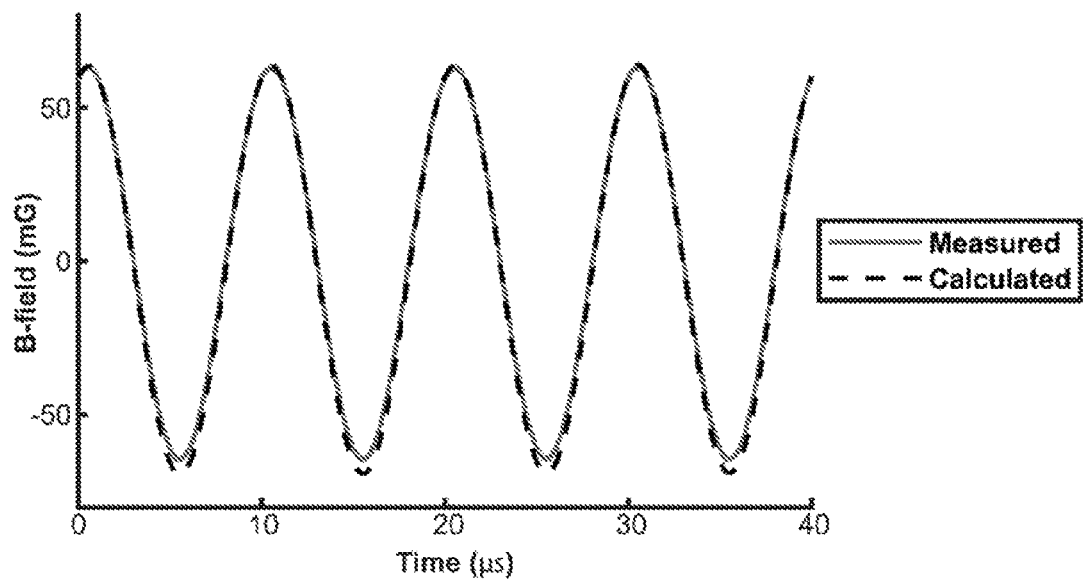
FIGS. 16A and 16B show comparison of measured and calculated B-field versus time.
Figure 16B:
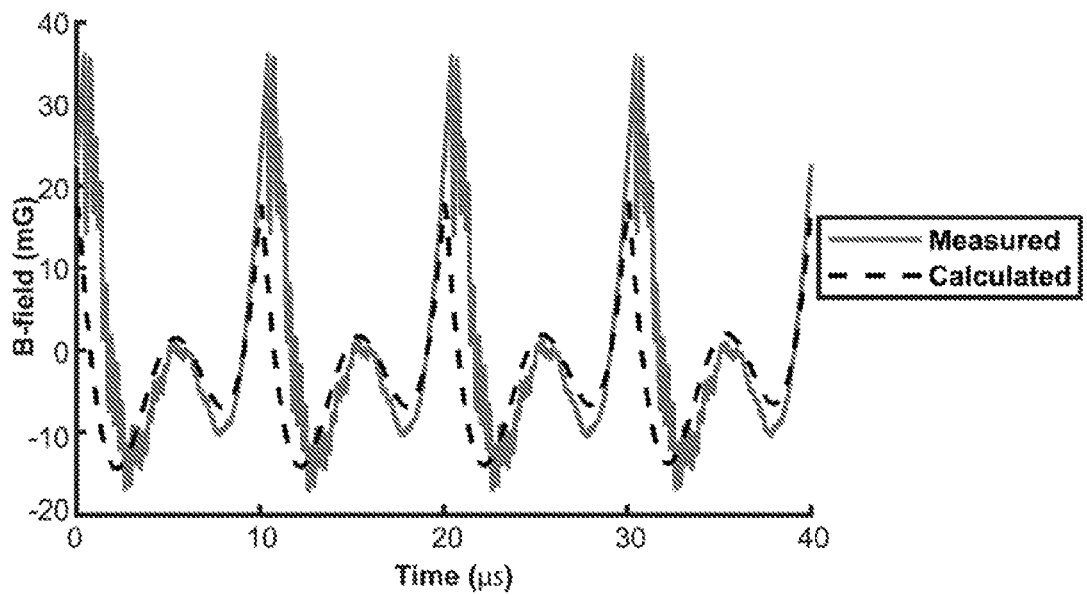

Each winding is treated as being an ideal loop of current and electric field and magnetic induction are calculated assuming that the respective contributions of each winding can be superposed at a specific location in space. The current through each loop was determined based on the current through the inductive branch of the circuit model shown in FIG. 13. A comparison of the calculated magnetic field versus the measured magnetic field (using a magnetic field probe, Magnetic Sciences, Model #M0162) for a sine wave is shown in FIG. 16A for the center position of the coil. FIG. 16B shows a comparison of the measured and calculated field for a sawtooth waveform. Although the measurement shows high frequency artifacts picked up by the probe, the model predicts that no such high frequency fields should exist so that these artifacts are likely related to the measurement. The discrepancy may be a result of capacitive coupling of the sensor with the probe during the measurement.

Characterization of Chemokine Gradients in the MBDM Assay

For the detailed characterization of chemokine gradients in the MBDM assay, a three-pronged approach was adopted. The diffusion coefficient was first estimated using the Stokes-Einstein equation, with the inherent assumption that the molecules of the fluorescently conjugated dye are spherical with a hydration radius of 2.3 nm for 10 kDa dextran (Watson, P. M. D., et al., (2013) BMC Neurosci. 14 (1):59). The diffusivity as determined by the Stokes-Einstein equation is given by:

$$D_0 = \frac{k_B T}{6\pi \eta R_H} \tag{S7}$$

where $D_0$ is the diffusivity in $m^2/s$, kB is Boltzmann's constant ($1.3806 \times 10^{-23}$ J/K), T is the temperature in K, $\eta$ is the viscosity in $N^{-s}/m^2$, and $R_H$ is the radius of the hydrated molecule. At 298 K, for $\eta = 8.9 \times 10^{-4}$ $N^{-s}/m^2$ and RH=2.3 nm, the value of $D_0$ given by this formula is 106.6 $\mu m^2/s$ ($1.066 \times 10^{-10}$ $m^2/s$).

The profiles of chemokine gradients were calculated using the Stokes-Einstein diffusivity by solving the one-dimensional, transient, diffusion equation and compared with experimental measurements of the chemokine gradient profiles (FIG. S5) over 12 hours using a 10-kDa FITC-conjugated dextran dye. The 1-D, transient diffusion equation is given by:

$$\frac{\partial C}{\partial t} = D_0 \frac{\partial^2 C}{\partial x^2} \tag{S8}$$

where C is the concentration of the dye, t is time, x is distance along the microchannel, and D0 is the diffusivity. Assuming the intensity of the fluorescing dye, I, is proportional to its concentration, Equation S8 can be re-written in terms of intensity:

$$\frac{\partial I}{\partial t} = D_0 \frac{\partial^2 I}{\partial x^2} \tag{S9}$$

Equation S9 was solved numerically using COMSOL Multiphysics 5.3a, to calculate the gradient profiles over a 12-hour period. The diffusivity $D_0$ was varied parametrically from $10^{-7}$ to $10^{-14}$ $m^2/s$, and the calculated profiles of I(x, t) were compared to measurements. A value of $D=1.74 \times 10^{-10} \pm 9.33 \times 10^{-11}$ $m^2/s$ was determined by comparison between calculations and experimental measurement with an R-squared>0.9. It can be seen that the experimentally determined diffusivity is on the same order as the theoretical value calculated using the Stokes-Einstein equation ($1.066 \times 10^{-10}$ $m^2/s$).

Based on the measured and calculated gradient profiles, we can be confident that for the duration of our migration experiments, the MBDM Assay is able to sustain stable gradients ensuring a chemotactic migratory response instead of a chemokinetic migratory response.

Calculation of Cell Mean Speed and Persistence in the MBDM Assay

To calculate persistence, the following protocol was followed for each cell tracked in a microtrack of the MBDM assay. A cell starts at position $P_t$ at time t. After a single time increment, dt, the cell moves to a new position, $P_{t+dt}$. The distance traveled during this time is the absolute difference in the two positions denoted as $L_i$:

$$L_i = |P_{t+dt} - P_t|$$

The total distance traveled is then the sum of all distances traveled during N time increments denoted as $L_t$. Additionally, the total time of travel is the number of time increments multiplied by the size of the time increments denoted as $T_t$.

$$L_t = \sum_{i=1}^{N} L_i$$

$$T_t = N \cdot dt$$

The displacement is simply the difference between the final and initial position:

$$L_d = |P_{Final} - P_{Initial}|$$

Therefore the mean speed can be calculated as follows:

$$\text{Mean Speed} = \frac{L_t}{T_t}$$

The persistence can be calculated as follows:

$$\text{Persistance} = \frac{L_d}{L_t}$$

Discussion

The effects of non-contact iEFs on cancer cell motility have been firmly established. Using a newly developed MBDM assay, average migration speeds and persistence of migrating MDA-MB-231 human breast adenocarcinoma cells have been measured and quantified under a variety of conditions. These conditions include with or without EGF gradients, presence of absence of iEFs, and presence and absence of an Akt inhibitor (MK2206), and all possible combinations of these parameters.

MDA-MB-231 cells were shown to increase their migration speeds when standalone iEFs were applied on average, anti-parallel to the direction of migration. However, in the same set of experiments that the migration speeds of these cancer cells showed no statistically significant change when the iEF was applied parallel to the direction of migration (FIG. 2). For the case of EGF-promoted motility, MDA-MB-231 cell migration was hindered irrespective of the direction of iEF in the modified transwell migration assay and contrary to what was reported for SCP2 cells (Ahirwar D K, et al. (2015) Sci Rep 5:11005). However, in the MBDM assay, EGF-promoted motility was hindered only by iEFs applied in the parallel direction. These results are significant when considering the physiological setting where epithelial cells can undergo epithelial-to-mesenchymal transformation. In this scenario, the endogenous fields are in a direction favoring metastatic invasion of the underlying stroma (Nuccitelli R (2003) Curr Top Dev Biol. 58 (2):1-26). For example, the endogenous EF in an epidermal layer (with an intact basement membrane) is directed away from the stroma and toward the epithelial layer and therefore the EF is inherently in a direction opposing migration. This situation corresponds to the conditions obtained here where the average migration speeds are observed to increase when iEFs are applied in the anti-parallel direction. These outcomes suggest that the endogenous EF, which is presumably in a direction to prevent (primarily) negatively charged microorganisms from settling on the epithelium, is actually favorable to promoting metastasis of a cancer cell from the epithelial layer (Nuccitelli R (2003) Curr Top Dev Biol. 58 (2):1-26).

The serine/threonine kinase Akt is well known to play a key role in many cellular functions including cell size and growth, proliferation, survival, glucose metabolism, genome stability, transcription and protein synthesis, and neo-vascularization (Nitulescu G M, et al. (2016) Int J Oncol 48 (3):869-885). The PI3K/Akt signaling cascade is also known to promote metabolism in response to extracellular signals, and could be a critical step in controlling cell migration. Previous reports with dcEFs have suggested that the PI3K/Akt pathway plays a vital role in directed galvanotactic migration (McCaig C D, et al. (2005) Physiol Rev. 85 (3):943-978; Zhao M, et al. (2006) Nature 442 (7101):457; Zhao M, et al. (2004) J Cell Sci 117 (Pt 3):397-405). Findings show that inhibition of Akt phosphorylation nullifies the directional response to iEFs of MDA-MB-231 cells. Additionally, the western blot analysis clearly shows that iEFs have no direct effects on Akt phosphorylation and total Akt levels. These results provide us with two insights into the possible mechanisms involving PI3K/Akt pathway in iEF sensing. Either Akt phosphorylation is necessary for these cells to sense and respond to externally applied iEFs or iEFs interact with proteins downstream of the Akt-signaling cascade, controlling the cell migration responses to these externally applied iEFs.

The EGF-EGFR axis is also known to trigger migration of MDA-MB-231 cells through the PI3K/Akt signaling cascade (Yang Y, et al. (2011) J Biomed Res. 25 (4):237-245). Hence, reduction in migration speeds of MDA-MB-231 cells in EGF-gradients upon treatment with MK2206 was not surprising. However, a surprising outcome was that combinatorial MK2206 treatment with parallel iEFs further downregulated migration speeds compared to the individual standalone iEF treatments. The migration speeds were well below the levels of untreated controls in this particular case. Additionally, the western blot analysis for total and phosphorylated Akt levels showed no direct effects of iEFs on EGF-treated MDA-MB-231s. As previously discussed, iEFs either increased the efficacy of MK2206 or iEFs and MK2206 acted concurrently along two independent pathways to suppress the motility of MDA-MB-231 under EGF-gradients.

iEFs affect the distribution of F-actin within the cell and lead to significant clustering of EGFR (Ahirwar D K, et al. (2015) Sci Rep 5:11005; Pu J, et al. (2007) J Cell Sci 120 (Pt 19):3395-3403). Previous work has also shown that EGFR signaling is essential for migration of breast cancer cells in the presence of current flow (Hennessy B T, et al. (2005) Nat Rev Drug Discov 4 (12):988-1004; Pu J, et al. (2007) J Cell Sci 120 (Pt 19):3395-3403). The actin distribution was not altered by iEFs in absence of EGF. The actin distribution was only affected for MDA-MB-231 cells when treated with parallel iEFs when migrating under EGF-gradients (recall that parallel iEFs also reduced average migration speeds in this case). iEFs also induced EGFR clustering in the absence of EGF, but based on western blot results for p-EGFR, no receptor activation was observed due to clustering. Consistent with previous reports (Ichinose J, et al. (2004) Biochem Biophys Res Commun 324 (3):1143-1149; Sako Y, et al. (2000) Nat Cell Biol 2 (3):168-172), EGF-induced clustering of EGFR was also observed. Therefore, while iEFs triggered receptor clustering, only ligand-induced receptor clustering resulted in receptor activation and downstream signaling. Western blot analysis of cells that received concurrent EGF and iEF treatment showed downregulation of p-EGFR without affecting EGFR clustering. In addition, there were found to be no changes to FAK activation in any case of iEF treatment. FAK is known to associate with EGFR (N-Terminal) and integrin (C-Terminal) and phosphorylation at Tyr 397 is necessary for this to happen (Sieg D J, et al. (2000) Nat Cell Biol. 2 (5):249). Further, it is known to interact with GTPases that control assembly and disassembly of actin cytoskeleton (Parsons J T, et al. (2010) Nat Rev Mol Cell Biol. 11 (9):633). Therefore, since we see iEFs have no effect on FAK activation or expression, changes observed in actin distribution and EGFR clustering are mediated independent of FAK. In summary, iEFs do not alter normal FAK function of MDA-MB-231 cells.

Both actin redistribution and EGFR phosphorylation need a constant supply of ATP. ATP is generated through cellular metabolism. It has previously been reported that application of 300 µV/cm static EFs (without current flow) directionally stimulate and inhibit glycolysis in astrocytes in culture (Huang R, et al. (1997) Bioelectromagnetics 18 (1):77-80). Therefore, possible links between altered metabolism with iEF treatment and results on hindered migration were investigated. iEFs downregulated the enzymatic activity of SDH (found within the mitochondria) of EGF-treated MDA-MB-231 cells but no changes were observed in the activity of LDH. It is known that SDH is part of the OXPHOS process in the mitochondria (during aerobic respiration) which can generate up to 36 ATP molecules per molecule of glucose whereas cytoplasmic glycolysis catalyzed by LDH only generates 2 molecules of ATP per molecule of glucose (Vander Heiden M G, et al (2009) Science 324 (5930):1029-1033). Previous work has shown that lowering of SDH activity directly correlates with lower actin filament formation, which was observed as well in the results reported here (Pathania D, et al. (2009) Adv Drug Deliv Rev. 61 (14): 1250-1275). Clearly, parallel iEFs prevent formation of actin focal points at the leading edges of MDA-MB-231 cells migrating under EGF-gradients. A possible mechanism that could explain these profound biological effects reported here could arise from iEFs inducing differences in electric potential between the cytoplasmic-side membrane and mitochondrial wall that are different from the control levels (i.e. without iEF). Any small change in this pre-existing potential difference could drive a redistribution of charge, which in turn could modify cytoplasmic NAD+/NADH ratios, affect metabolic pathways that are necessary for cell migration, and affect intracellular signaling including the PI3K/Akt pathway. Another possible mechanism involving mitochondria could be through $Ca^{2+}$ ions, as it is known that $Ca^{2+}$ ions depolymerize actin through calcium activated actin-binding proteins such as gelsolin (Weeds A (1982) Nature 296 (5860):811; Revenu C, et al. (2004) Nat Rev Mol Cell Biol. 5 (8):635). Mitochondria can act as intracellular sources of $Ca^{2+}$ ions (Bygrave F L (1978) Biol Rev Camb Philos Soc. 53 (1):43-79) and in addition, mitochondrial trafficking is known to occur near lamellipodia (67-69). While it appears likely that iEFs are potentially interfering with the energetics of cell migration, further studies are required to determine a mechanism that can explain all the results presented here and reported earlier with iEFs (Ahirwar D K, et al. (2015) Sci Rep 5:11005).

The bioelectric effects reported here arise from EFs induced by time-varying magnetic fields (Faraday's law). While other non-contact fields such as tumor treating fields (TTFs) utilize much larger EFs (~1 V/cm) (Kirson E D, et al. (2004) Cancer Res 64 (9):3288-3295), our iEFs are only on the order of 100 µV/cm or less. Previous reports have speculated as to how such weak fields (<100 µV/cm) can have any biological effects (Weaver J C & Astumian RD (1990) Science 247 (4941):459-462; Barnes F S (1992) Bioelectromagnetics 13 (S1):67-85). A simple estimation of the EF required to alter the cellular membrane potential is given by $\Delta\psi = 3/2\ Er$, where $\Delta\psi$ is the change in membrane potential, E is the applied EF, and r is the radius of the cell. Based on a minimum membrane potential change of 1 mV and a cell radius of 10 µm, the EF required is calculated to be ~670 mV/cm. While the magnitude of the iEFs used in this study is too weak to cause substantial changes to membrane potential, it is possible that there could be a compounding effect due to the cyclic and spatially coherent nature of the iEF. Since the wavelength of the iEFs in this study is far greater than the size of any cell, changes to the magnitude of the iEF would be sensed simultaneously by all membrane proteins. It is possible that a subtle, simultaneous change in similar membrane proteins could lead to a significant cellular response over time (Weaver J C & Astumian R D (1990) Science 247 (4941):459-462). Using the equation for a spherical cell from Weaver & Astumian (1990) (73), a 21 µV/cm EF at 100 kHz would be able to elicit a response from a cell with 10 µm radius within 30 minutes. Unfortunately, this estimate requires multiple simplifying assumptions and ultimately requires identification of the cellular component or components that are being acted upon. To that end, the results from this study represent a significant step toward isolating the coupling mechanism between cells and iEFs.

In summary: (1) iEFs applied in the anti-parallel direction in the absence of EGF gradients increased the average migration speeds of MDA-MB-231s, (2) Inhibition of Akt impaired the ability of MDA-MB-231s to sense the directionality of iEFs, (3) iEFs potently hinder EGF-stimulated MDA-MB-231 cell motility, (4) Combined treatment with iEFs and an Akt inhibitor (MK2206) significantly reduced cancer cell migration speeds independent of EGF-gradients, (5) iEFs alter the distribution of F-Actin in MDA-MB-231s migrating under EGF-gradients, (6) iEF treatment induced EGFR clustering inside MDA-MB-231 cells, (7) iEFs down-regulated the phosphorylation of EGFR, and (8) iEFs inhibited SDH enzymatic activity of EGF-treated MDA-MB-231s without altering their LDH activity. Taken collectively, this body of results represents a significant step toward identifying how low frequency (<1 MHz) iEFs interact with mammalian breast cancer cells and the possible governing mechanisms controlling their migratory responses. The results presented here could lay the foundation for exploring non-contact and new therapeutic approaches that may be used in a stand-alone manner or in conjunction with chemotherapy such as an Akt inhibitor based strategy.

Materials and Methods

Cell Lines and Reagents

MDA-MB-231 breast adenocarcinoma cells stably expressing GFP (Song J W, et al. (2009) PloS one 4 (6):e5756) (gift from Luker Lab, University of Michigan, Ann Arbor) were cultured in DMEM (Life-Technologies, 11995073) supplemented with 1% penicillin-streptomycin-glutamine (100 µg/mL, Life Technologies, 10378016), and 10% fetal bovine serum (FBS) (Atlas Biologicals, EF-0500-A, E27D17A1). For all experiments reported in this paper, migration media was used that had 0.1% FBS without any additional exogenous growth factors; the rest of the supplements remained the same as their respective growth media.

Helmholtz Coil

A Helmholtz coil was in-house custom designed to accommodate application of iEFs using a Nikon Eclipse TE2000-U microscope (Nikon Instruments Inc.) to generate time-lapse images of cells located inside of a 6-well culture plate (FIGS. 1A-1C). The frame of the coil was designed to fit into the same multiwell plate holder already fabricated for the microscope stage. The condenser of the microscope limited the vertical range of the coil while the focal length of the objectives limited the thickness of the coil. Additionally, in order to visualize the cells inside the wells, sections of the coil were separated to create windows in order to image the six wells. This required gaps between windings leading to the implementation of a Helmholtz style coil, as can be seen in FIG. 1. The rectangular cross section of the coil was designed so that a multi-well plate could be easily inserted in its bore. With these constraints, the final designed coil comprised four individual segments in series with a separation of 12 mm for the viewing windows. Each segment measured 22 mm in height and 91 mm in width. The depth of the outer and inner segments were 18 mm and 28 mm respectively (FIG. 13B). Each coil segment had approximately 10 layers with the outer (FIG. 13A, Sub-Coil 1 and Sub-Coil 4) segments having 25 turns per layer and the inner (FIG. 13A, Sub-Coil 2 and Sub-Coil 3) segments having 40 turns per layer.

The frame of the coil was designed in SolidWorks and 3D printed with acrylonitrile butadiene styrene as the material. The coil was wound by hand with 32 AWG insulated copper wire (0.202 mm diameter). The turns were separated to try to prevent proximity effects from increasing the AC impedance of the coil. The ends of the wound wire were soldered to a BNC cable with wire leads.

The coil inductance and resistance were measured using an LCR meter (Keysight U1733C) at 100 kHz. The capacitance was inferred from measurement of the resonant frequency of the coil as determined from the frequency response (Ahirwar D K, et al. (2015) Sci Rep 5:11005). A simple circuit element model of the coil was developed with measured and calculated parameters (Ahirwar D K, et al. (2015) Sci Rep 5:11005). This model was used to infer the conduction current through the Helmholtz coil. Using the geometry of the coil, the vector potential was calculated versus position and time, and analytically differentiated with respect to time to calculate the iEF. The magnetic induction ($\vec{B}$) was calculated using the curl of the vector potential, A and the calculated conduction current in the coil, I(t). The calculated values of the magnetic induction were validated against measurements of $\vec{B}$ using a fluxgate sensor (Magnetic Sciences, Model #MC162). The sensor was placed at the center of the coil and the magnetic induction trace was recorded on an oscilloscope (Agilent DSO-X 2014A).

Microfluidic Bi-Directional Migration Assay

The MBDM assay was designed to have three ports separated by 700 µm long arrays of parallel microtracks (FIG. 1D). The dimension of each port was 50 mm×15 mm. Cells were seeded in the center port and the top and bottom ports were designated as cell collection port and/or chemokine source reservoir port depending on the experimental condition. Microchannels were designed to have a square cross-section of 20 µm×20 µm. The cross-section dimensions were on the same order as the size of single cells and mimic the dimensions of pre-existing microtracks available to cells in-vivo (Kraning-Rush C M, et al. (2013) Integr Biol (Camb). 5 (3):606-616). Moreover, these migratory tracks are representative of physiologically relevant matrix metalloproteinase independent cancer-cell migration mode during metastasis (Friedl P & Alexander S (2011) Cell 147 (5):992-1009; Wolf K, et al. (2009) Semin Cell Dev Biol. 20 (8):931-941; Friedl P & Wolf K (2003) Nat Rev Cancer. 3 (5):362; Wolf K, et al. (2007) Nat Cell Biol. 9 (8):893; Wolf K, et al. (2003) J Cell Biol. 160 (2):267-277). The bi-directional design of this assay allows cells to migrate in either direction from the seeding port and provides a better understanding and quantification of the directional bias of external cues such as chemokine gradients and the directional effects of applied iEFs. The large ports for cell seeding ensure uniform seeding density, excellent cell viability, and repeatability.

The designs for transparency masks were created using AutoCAD-2014 and the final masks were printed at 25000 DPI (CAD/Art Services, OR). A standard photolithography process (Whitesides G M, et al. (2001) Annu Rev Biomed Eng. 3 (1):335-373; Qin D, et al. (2010) Nature protocols 5 (3):491; Weibel D B, et al. (2007) Nat Rev Microbiol. 5 (3):209; Kane R S, et al. (1999) Biomaterials 20 (23):2363-2376) was used to fabricate the silicon masters wherein a 20 µm thick layer of SU-8 2025 (Spin Speed: 3000 rpm; Spin Time: 90 sec) was spin coated on a piranha cleaned test-grade silicon wafer (University Wafer). The coated wafer was then exposed to UV light through the transparency mask, which resulted in crosslinking of the photoresist imprinting the design on the wafer. The exposed wafers were treated with SU-8 developer that washed away the soft uncross-linked SU-8 resulting in formation of the negative pattern of the required micro-channel geometry on the wafer. The wafer was then cleaned with isopropyl alcohol solution and passivated for 30 minutes in a fume hood with tridecafluoro-1,1,2,2-tertahydrooctyl)-1-trichlorosilane (United Chemicals Ltd., T2492-KG). Salinization passivates the wafer surface and prevents it from sticking to the polydimethylsiloxane (PDMS). All the processing until this stage was done in a Class 100 Cleanroom. A technique called replica molding was used to get the final micro-channel based migration assay from the silicon master (81). A 10:1 solution of PDMS Base Elastomer and Cross-linker (Sylgard 184 Silicone Elastomer, Dow Corning Corporation) was poured over the wafer, degassed, and cured at 65° C. for two hours. Cured PDMS was peeled off the silicon master and was cut into 20 mm×20 mm square pieces. For fabricating the seeding and the collection ports in the devices, we punched holes using a 4 mm biopsy punch; these devices were then plasma oxidized and irreversibly bonded to cured PDMS in 6-well culture plates. The 6-well culture plate was sterilized in high-intensity UV light and each device was treated with 10 µg/mL of fibronectin and incubated at 37° C. for 90 minutes; PDMS absorbed the fibronectin and made the surface conducive for cell attachment and growth.

EGF Gradient Characterization

Figure 11A:
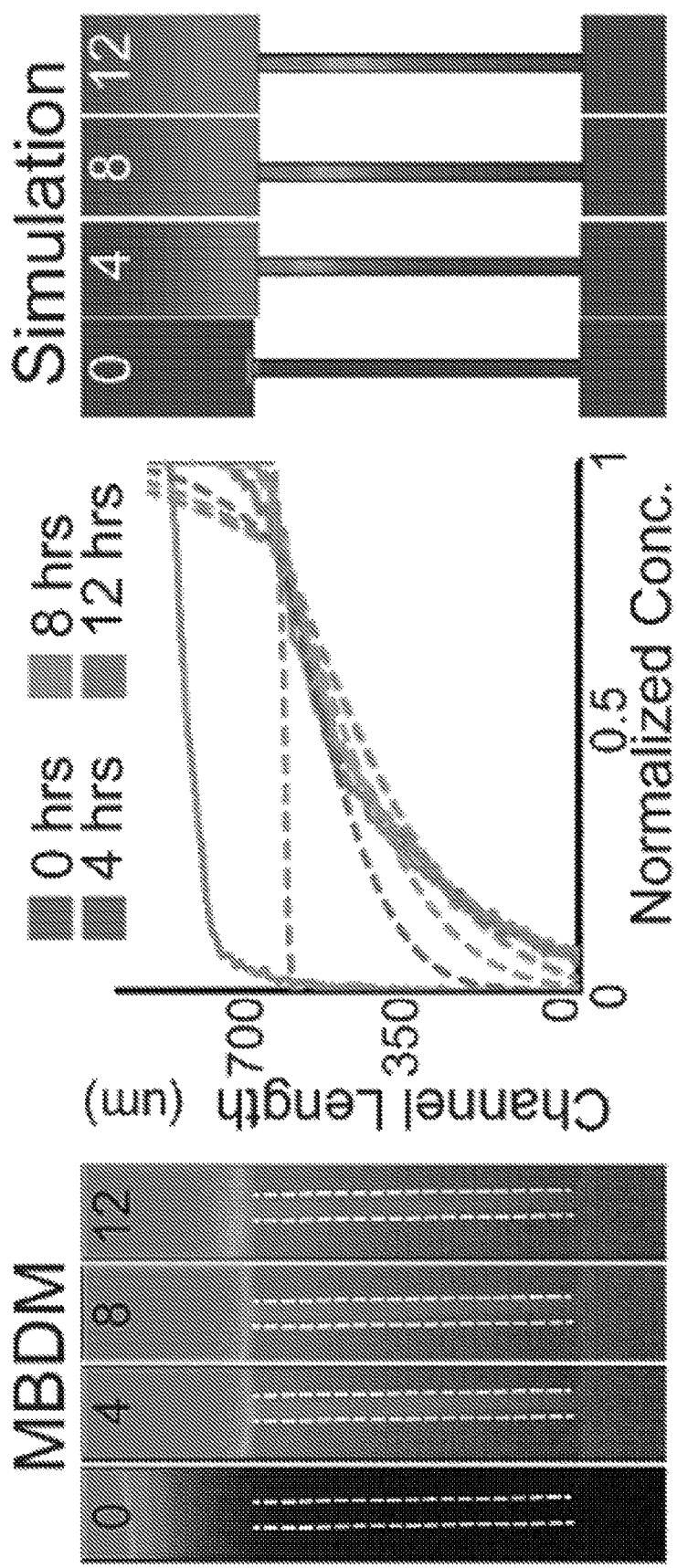
FIGS. 11A to 11F show chemokine gradient characterization.
Figure 11C:
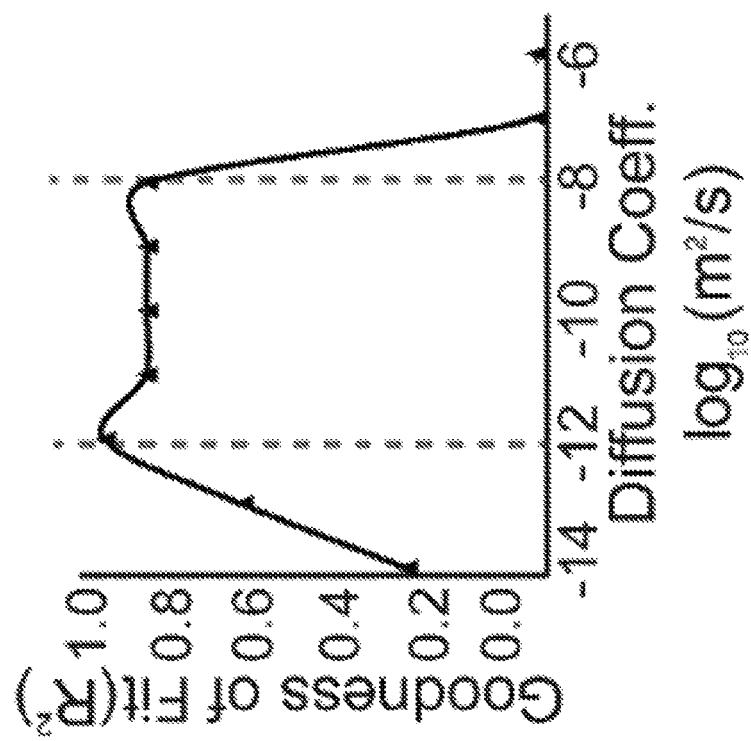
Figure 11B:
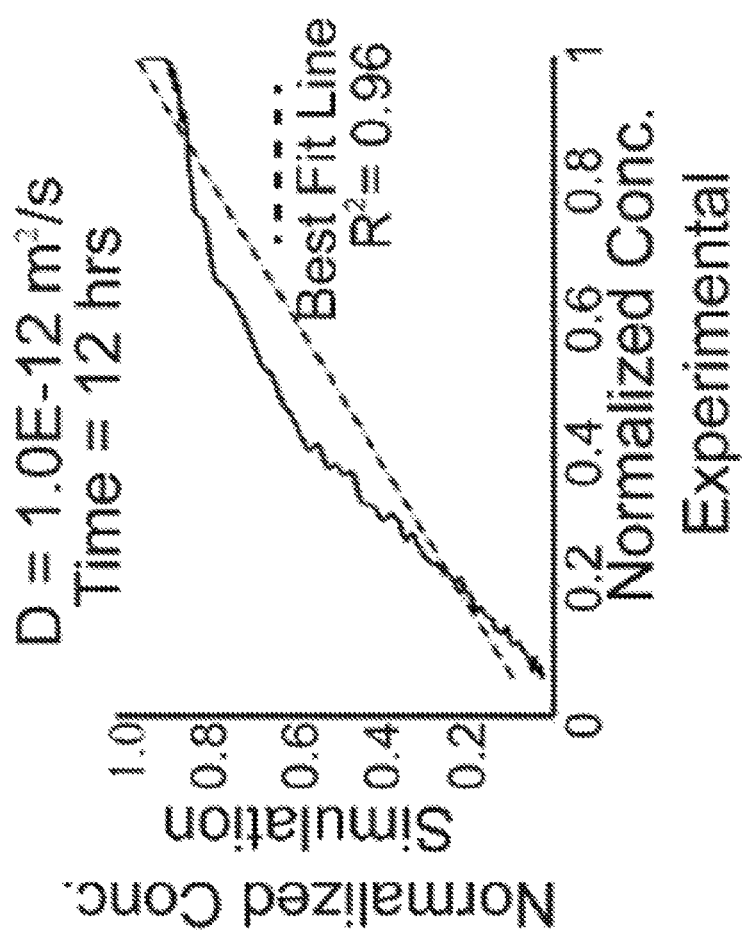
Figure 11F:
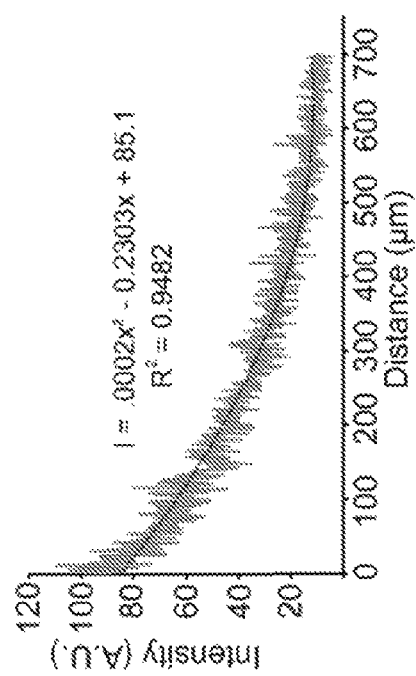
Figure 11E:
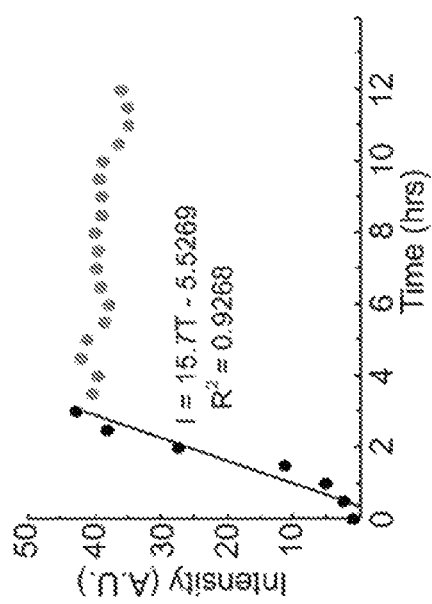
Figure 11D:
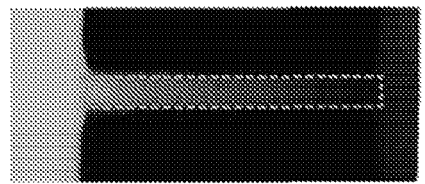

To characterize the biomolecular gradient profile in the MBDM assay, 10 kDa FITC conjugated dextran was used as a surrogate fluorescent tracer for EGF which has a molecular weight of ~6 kDa (Taylor J M, et al. (1970) Proc Natl Acad Sci U S A. 67 (1):164-171). FITC-dextran was prepared in 1×PBS to a concentration of 1 mg/mL. The seeding and the bottom collection ports on the device were filled with 1×PBS and the top port (in this case the chemokine port) was filled with 1 mg/mL FITC-Dextran solution while ensuring that no fluid flow takes place from top port to the middle or bottom port in order to establish purely mass transfer (diffusion) based gradients. The device was then monitored under a stereo microscope (Nikon Instruments Inc.) for 12 hours at intervals of 5 minutes between each frame (FIG. 11A). Gradient profiles and diffusion coefficients were then quantified using both finite volume numerical simulation in COMSOL Multiphysics 5.3a and NIH ImageJ Image Processing Software (FIG. 11B-11F, Eq. S7-S9).

Cell Seeding and Migration

Cells were washed in culture plates with 1×PBS solution, treated with 0.05% trypsin-EDTA solution (Sigma-Aldrich), and then counted using a hemocytometer. Cells ($2 \times 10^5$) suspended in migration media were seeded in the middle port (seeding port) with an extremely small flow from the collection ports to the seeding port, which equilibrated in less than 15 minutes. The cells inside the devices were then incubated for 12 hours in migration media following which the media was aspirated and replaced with new media based on the experimental conditions. For experiments with growth factor stimulation, the migration media was supplemented with EGF (25 ng/mL) and was introduced in only one of the two collection ports. Devices were incubated for another 36 hours in culture media and refreshed every 12 hours. Cell migration was then observed using a time-lapse scope in a live-cell chamber for 12 hours. In the case of experiments involving the Akt inhibitor, the media was supplemented with 2.5 µM of MK2206 immediately before the 12 hour time-lapse.

Transwell Migration Assay

Transwell permeable supports that have 6.5 mm diameter inserts of polycarbonate membrane with 8 µm diameter pore size (Corning, CLS3422) were used in the experiments reported here. Each transwell insert was coated with 80 µL of 10 µg/mL fibronectin solution (in 1× phosphate buffer saline (PBS), Corning Inc., 354008) and left to dry for 12 hours. Cells were simultaneously serum starved in migration media for 12 hours. Following this step, the cells were removed using 0.05% trypsin-0.02% EDTA solution (Sigma-Aldrich, 59417C) and handled exclusively in migration media. Cell suspensions with a concentration of $1 \times 10^6$ cells/mL were prepared and 150 µL of this media ($1.5 \times 10^5$ cells) were plated in the top chamber of each transwell insert and the bottom chamber was filled with 600 µL of migration media or EGF supplemented migration media (100 ng/mL EGF). After 8 hours, the cells were fixed using a standard HEMA 3 solution kit (Fisher Scientific, 23-123869) and imaged using a Stereo Microscope (Leica Microsystems Inc.). Cell migration numbers were then quantified using a custom MATLAB script as described in Image Acquisition and Processing. Cell migration without growth factors and without iEFs served as controls and all the other conditions were normalized with respect to these controls.

Imaging of F-Actin in the Microfluidic Bi-Directional Microtracks Assay

Cells in the devices were fixed in 3.7 (wt/wt) paraformaldehyde solution for 30 minutes. They were subsequently washed with 1×PBS three times. For F-actin labeling, we blocked the cells for 60 minutes in blocking buffer (0.1% Triton-X and 5% donkey serum in 1×PBS). Cells were then treated with Alexa Fluoro® 488-conjugated or 555-conjugated phalloidin for 60 minutes (1:40, ThermoFisher), again followed by a 1×PBS wash (three times, 10 minutes each). Finally, the nuclei were labelled with 4',6-diamidino-2-phenylindole (DAPI) (1:5000, Sigma-Aldridge, D9542). The nuclei labelling was followed by a final 1×PBS wash (three times, 10 minutes each) and the devices were left overnight in 1×PBS at 4° C.

Immunofluorescence Staining of EGFR and F-Actin

In these experiments, $1\times10^4$ cells were cultured on fibronectin-coated (10 µg/mL), 22 mm #1 glass slides. Cells were allowed to adhere for 12 hours in growth media. Cells were then serum starved in migration media for another 12 hours. The media was then replaced with fresh migration media. For EGF treated cases, the migration media was supplemented with 25 ng/mL of EGF. Cells were then either incubated with or without iEFs for 12 hours. The direction of the applied fields was noted for samples treated with iEFs. The cells were fixed with 3.7% (wt/vol) paraformaldehyde solution for 20 minutes and then washed three times with 1×PBS (5 minutes each). We then blocked the cells for 60 minutes using a blocking buffer (0.1% Triton-X 100, 5% goat serum in 1×PBS). The cell samples were treated with the primary EGFR antibody (1:1000, MA5-13319, Thermo-Fisher, diluted in blocking buffer) and left overnight at 4° C. The cell samples were then washed three times with 1×PBS supplemented with 0.1% Tween-20 (1×PBST) for 15 minutes each. The secondary antibody (Anti-Rabbit Alexa Fluro®488, 1:2000 in blocking buffer) was then added and the cells stored in the dark at room temperature for 60 minutes followed by three 1×PBST washes for 15 minutes each. ActinRed™ 555 ReadyProbes® Reagent (Thermo-Fisher) was used based on manufacturer instructions to tag the F-actin cytoskeleton. The samples were then washed three times with 1×PBST for 15 minutes each. Finally, the cell nucleus was stained with DAPI (Sigma-Aldrich, 1:5000 in DI water, D9542) and samples were washed three times with 1×PBST for 15 minutes each. The samples were then mounted using Fluoromount-G® (Southern Biotech), allowed to dry overnight at room temperature, and then imaged using the LSM 700, a high-resolution laser scanning confocal microscope (ZEISS Instruments Inc.).

Western Blot

For these experiments, $1\times10^6$ cells/well were plated in 6-well plates in growth media for 12 hours followed by migration media for another 12 hours. Fresh migration media was added to the top three wells in each plate (1, 2, 3) while EGF (25 ng/mL) and supplemental migration media were added to the bottom three wells (4, 5, 6). One of the cell-containing 6-well plates was then treated with iEFs for 12 hours. Immediately after treatment, the plates were placed on ice and each well was then washed three times with 1× tris-buffered saline (TBS, Corning Inc.) solution. TBS was aspirated out and 1 mL ice-cold radioimmunoprecipitation assay (RIPA) buffer, supplemented with a protease inhibitor and a phosphatase inhibitor, was added to each well. Cells were scraped out using a cold plastic cell scraper and the cell suspension was transferred into a pre-cooled microcentrifuge tube. The cell suspension was then spun at 16000 g for 20 minutes in a 4° C. precooled centrifuge. The centrifuge tubes were placed on ice and the supernatants were transferred to fresh tubes and kept on ice. The pellet at the bottom of each microcentrifuge tube was discarded. Protein in each tube was estimated against a standard bovine serum albumin (BSA) solution (1.42 mg/mL) using the DC™ Protein Assay Kit II (Bio-Rad, 500-0112). 50 µg of total protein was then collected, mixed with 10 µL dye (Invitrogen, NP0007) and 5 µL reducing agent (Invitrogen, NP0009) from each condition, and loaded on to a 4-12 gradient gel (Invitrogen, NP0335BOX). The gel was then placed in the running buffer (Invitrogen, NP0001, 1:20 dilution in DI water) at 120 V for approximately 2 hours. Gels were then placed in a transfer buffer (Tris/Glycine Buffer, Bio-Rad, 161-0771—diluted to 1× with 20% methanol in DI water) for 5-10 min following which the transfer sandwich was prepared. The sandwich was placed in a transfer tank and run at 18 V for 90 minutes. The blot was then washed with 1×TBST (1×TBS with 0.1% Tween-20) three times for 15 minutes each. The blot was blocked with 5% BSA in TBST solution for 1 hour at room temperature. Primary antibodies (p-EGFR (1:1000, Cell Signaling Technology, 4407S, 3777S), p-Akt (1:2000, Cell Signaling Technology, 9271S), p-FAK (1:1000, Thermo-Fisher, 700255), t-EGFR (1:200, Santa Cruz, sc-03-G), t-Akt (1:200, Santa Cruz, sc-8312), t-FAK (1:1000, Cell Signaling Technology, 3285S), and GAPDH (1:1000, Cell Signaling Technology, 5174S)) were then prepared in the blocking solution (5% BSA in TBST) and left overnight on a rocker at 4° C. The blots were washed three times for 15 minutes each with 1×TBST solution. Secondary antibody (1:2000, GE Healthcare, LNA934V/AH) was prepared in the blocking solution and the blots were treated with the secondary antibody solution for 2 hours at room temperature followed by three 15-minute washes with TBST solution. Blots were then treated in the dark with the Pierce® ECL Western Blotting Substrate (Thermo Scientific, 32209) for 5 minutes and then developed using standard solution in an X-ray room based on protocol provided by the manufacturer.

Image Acquisition and Processing

Images from experiments with the transwell migration assays were taken using a stereo microscope (Leica Microsystems Inc.) after fixation and staining of the cells using the HEMA 3 solution kit (Fisher Scientific). Images were taken at a magnification such that the entirety of the transwell membrane was within the frame. The images were then imported into MATLAB and analyzed using a custom code (MATLAB script). The script splits the images into RGB components and uses the Otsu method (Otsu N (1979) IEEE Trans Syst Man Cybern. 9 (1):62-66) for setting the background threshold intensity so that the cell can be distinguished from the background using the inverse of the green channel. All groups of pixels with connectivity of at least eight pixels were identified as single objects. To account for clustering of cells, each object's area was divided by the average area of a cell. The average area of a cell was determined from the mean of manual measurements of approximately 20 isolated cells for each case. The count from each cluster was rounded to the nearest integer value and summed to obtain the total cell count. The plotted values are all normalized to the control conditions for each case.

Time-Lapse Movies

The time-lapse movies were acquired using a Nikon Eclipse TE2000-U microscope (Nikon Instruments Inc.) in 5-minute intervals between images for 12 hours using a 10× objective (FIG. 5B). The on-stage incubator maintained $CO_2$ levels at 5% and the temperature at 37° C. for the duration of the experiment. The time-lapse movies were analyzed using the MtrackJ plugin (Meijering E, et al. (2012) Methods Enzymol. 504 (9):183-200) in Fiji (Schindelin J, et al. (2012) Nat Methods. 9 (7):676) to determine average cell speed, distance travelled, and displacement data.

Actin Immunofluorescence in the MBDM Assay

Actin immunofluorescence images were acquired using a Nikon TE200 epifluorescence microscope (Nikon Instruments Inc.) under a 20× objective. The immunofluorescence images were quantified using custom MATLAB scripts. The custom MATLAB script calculated the geometric center for an individual cell, i.e. the arithmetic mean of the locations of all pixels comprising the cell area. Then the distance from this geometric center and angle ($0° \leq \theta \leq 360°$) of every pixel relative to a horizontal axis ($\theta=0°$) was calculated. The cell was then divided into 360 equal sectors each with a sector angle of 1°. Each 1° sector was defined as an individual bin. Irrespective of the cell shape, it is considered a unit circle for the purposes of this calculation. A moment of intensity is calculated for individual pixels and this value is summed for all the pixels in every individual sector. This total value is normalized to the total number of pixels in that sector. This method is summarized in the following equation:

$$J = \frac{1}{N}\sum_{k=1}^{N} r_k^a I_k$$

where J is the moment of intensity for an individual bin, N is the total number of pixels in the bin, rk is the distance of pixel k from the centroid, a is a weighting factor (cell aspect ratio), and lk is the intensity of pixel k. Finally, all the 360 individual bins are normalized with respect to the maximum value of the summed moments and the normalized value for each sector is plotted on the unit circle giving a visual and quantitative representation of the distribution of intracellular actin. An index referred to here as the polarization ratio (PR), is used to determine whether the intracellular actin is distributed in a preferential way. The PR is defined as the ratio of the number of occurrences of high (0.8) normalized summed moments of intensities in the sectors $75° \leq \theta \leq 105°$ and $255° \leq \theta \leq 285°$, to the total occurrences of high (0.8) normalized summed moments of intensities.

$$PR = \frac{\sum_{\theta=75°}^{105°} N_\theta(\mathcal{J}(\theta) > 0.8) + \sum_{\theta=255°}^{285°} N_\theta(\mathcal{J}(\theta) > 0.8)}{\sum_{\theta=0°}^{360°} N_\theta(\mathcal{J}(\theta) > 0.8)}$$

where $\bar{j}(\theta)$ is the normalized moment of intensity at the angle $\theta$, $N_\theta$ ($\bar{j}(\theta)$) is the number of bins, $\Sigma^{360°}_{\theta=0°} N_\theta(\bar{j}(\theta)>0.8) \geq 1$. A PR of 1 thus implies that all the intracellular F-actin is primarily localized at the leading and/or trailing edges of the cell whereas a value of 0 indicates no localization at the leading and trailing edges. A PR of 0.167 implies an even distribution of actin throughout the cell. Only single-isolated cells that were migrating inside the channels were analyzed using this approach.

Immunofluorescence Staining of EGF Receptor and F-Actin

Images were acquired using the LSM700 laser scanning confocal microscope (Carl Zeiss Microscopy GmbH., Germany) with a 63× oil objective. Laser power was set to 5.0 V and the gain was set to 550 (DAPI channel, nucleus), 600 (Alexa Fluor® 488, EGFR), and 600 (Alexa Fluor® 555, Actin) for all samples.

Western Blots

Western Blot analysis of lysates was done as described in ref. (88).

Quantification of LDH and SDH Activity $1 \times 10^6$ cells/well were plated in 6 well plates in growth media for 12 hours followed by migration media (0.1% FBS) for an additional 12 hours. Then, fresh migration media was added to the top three wells in each plate (1, 2, 3) while EGF supplemental migration media (25 ng/mL) were added to the bottom three wells (4, 5, 6). One of the cell-containing 6-well plates was then treated with iEFs for 12 hours. After treatment, the plates were placed on ice and each well was then washed three times with PBS solution (1×PBS, Corning Inc., 354008). The LDH activity assay kit (Sigma-Aldrich, MAK066) and the SDH activity colorimetric assay kit (Sigma-Aldrich, MAK197) were used to quantify LDH and SDH activity respectively. The PBS solution in each well was aspirated and replaced with either 500 µL of LDH assay buffer or 100 µL of SDH assay buffer. The cells were then placed in −80° C. for 15 minutes. After thawing, the cells were then scraped out using a plastic cell scraper and the cell suspension was transferred into a microcentrifuge tube. The pellet at the bottom of each microcentrifuge tube was discarded. Protein in each tube was estimated against a standard BSA solution (1.42 mg/mL) using the DC TM Protein Assay Kit II (Bio-Rad, 500-0112). For quantification of LDH and SDH, the protocols provided by the supplier were followed. For LDH, the supernatants were diluted by 1000 to obtain kinetic curves in the linear range of the standard curve and for SDH the supernatants were not diluted. The final activity levels were divided by normalized protein content.

Statistical Analysis

The sample populations were compared for the mean migration speed data and the cell persistence data using the unpaired, two-tailed Student t test. A p-value<0.05 was used as the threshold for statistical significance. The data points on the figures represent the mean values and error bars depict standard error in mean (SEM).

For the intracellular actin distribution analyzed using the PR, the sample populations were compared using the non-parametric Wilcoxon Test for each pair. A p<0.05 was used as the threshold for statistical significance. The data points on the box plots represent the minimum value, 1st quartile, median, 3rd quartile, and maximum value of PR for each condition.

For Western blot analysis, sample populations were compared using unpaired, two-tailed Student t-test. A p-value<0.05 was used as the threshold for statistical significance. The data points on figures represent the mean values and error bars depict standard error of the mean (SEM).

For the LDH and SDH calorimetric assay, sample populations were compared using unpaired, two-tailed Student t-test. A p-value<0.05 was used as the threshold for statistical significance. The data points on the figures represent the mean values and the error bars represent standard error of the mean (SEM).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A microfluidic device for assessing cell migration, comprising
   a cell migration chamber comprising an optically transparent material coated with a cell migration substrate; and
   a Helmholtz coil electromagnet configured to produce an induced electric field across a length of the cell migration chamber, thereby defining a positive end of the cell migration chamber and a negative end of the cell migration chamber,
   wherein the cell migration substrate is fabricated into microtracks comprising microchannels about 1 to 100 μm in width, the microchannels substantially parallel with the induced electric field.

2. The device of claim 1, comprising a cell port in the middle of the cell migration chamber configured to receive cells, a first media port at the positive end of the cell migration chamber, and a second media port at the negative end of the cell migration chamber, a plurality of microtracks fluidly connecting the cell port to the first media port, and a plurality of microtracks fluidly connecting the cell port to the second media port.

3. The device of claim 1, wherein the cell migration substrate comprises collagen.

4. The device of claim 1, wherein the Helmholtz coil is spaced to create a viewing window for the cell migration chamber.

5. The device of claim 1, wherein the device is sized to fit on a microscope stage.

6. The device of claim 1, comprising a plurality of cell migration chambers, wherein the Helmholtz coil electromagnet produces the induced electric field across each of the plurality of cell migration chambers.

7. The device of claim 1, wherein the electromagnet produces an electric field of about 1 to 100 uV/cm.

8. The device of claim 1, wherein the optically transparent material comprises PDMS.

9. The device of claim 1, further comprising a microscope positioned to generate time-lapse images of cells in the cell migration chamber.

10. The device of claim 1, wherein the Helmholtz coil electromagnet comprises a series of coils, adjacent coils separated by at least one viewing window.

11. The device of claim 10, wherein the cell migration chamber is positioned within the series of coils, at least a portion of the microtracks aligned with the at least one viewing window.

12. The device of claim 11, wherein a microscope is positioned adjacent to a viewing window, the microscope configured to generate time-lapse images of the cell migration chamber.

13. A method for assaying cells, comprising
   (a) providing the device of claim 2;
   (b) loading cells into the cell port;
   (c) loading a first medium into the first media port and a second medium into the second media port, wherein at least one of the first medium or the second medium comprises a chemokine in an amount to produce a chemokine gradient;
   (d) activating the electromagnet to produce an electric field across the cell migration chamber; and
   (e) imaging the cells to measure the dual effect of the chemokine and the electric field on the cells.

14. The method of claim 13, wherein the cells are cancer cells.

15. The method of claim 14, wherein the cancer cells are breast cancer cells.

16. The method of claim 15, wherein the chemokine is epidermal growth factor (EGF).

17. The method of claim 13, further comprising repeating steps (a) to (e) with the chemokine gradient going in the opposite direction.

18. The method of claim 13, further comprising loading a candidate agent into one of the cell port, first media port, or second media port to evaluate the effect of the candidate agent on cell migration.

19. The method of claim 18, wherein the candidate agent comprises a candidate inhibitor of metastasis.

* * * * *